(12) United States Patent
Brown et al.

(10) Patent No.: US 11,628,126 B2
(45) Date of Patent: Apr. 18, 2023

(54) CLEAR CLEANSING COMPOSITION

(71) Applicant: The Procter & Gamble Company, Cincinnati, OH (US)

(72) Inventors: Mark Anthony Brown, Union, KY (US); Gemma Zoe Braganza, Singapore (SG); Junichi Yokogi, Singapore (SG); William Randal Belcher, Bellbrook, OH (US); Linda Sue Reed, West Chester, OH (US); Jorge Max Sunkel, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 36 days.

(21) Appl. No.: 16/432,371

(22) Filed: Jun. 5, 2019

(65) Prior Publication Data
US 2019/0365611 A1 Dec. 5, 2019

Related U.S. Application Data

(60) Provisional application No. 62/680,718, filed on Jun. 5, 2018.

(51) Int. Cl.
*A61K 8/00* (2006.01)
*A61K 8/02* (2006.01)
(Continued)

(52) U.S. Cl.
CPC .............. *A61K 8/0241* (2013.01); *A61K 8/25* (2013.01); *A61K 8/26* (2013.01); *A61K 8/29* (2013.01);
(Continued)

(58) Field of Classification Search
CPC ........ A61K 8/0241; A61K 8/25; A61K 8/463; A61Q 5/02
See application file for complete search history.

(56) References Cited

U.S. PATENT DOCUMENTS

| 1,094,935 A | 4/1914 | Schenck et al. |
| 2,326,733 A | 8/1943 | Fisher |
| (Continued) | | |

FOREIGN PATENT DOCUMENTS

| AU | 2012337567 B2 | 4/2017 |
| CA | 2143558 A1 | 8/1996 |
| (Continued) | | |

OTHER PUBLICATIONS

"Herbal Essence Shampoo", Mintel, Jun. 1, 2014, 2 pages.
(Continued)

*Primary Examiner* — Necholus Ogden, Jr.
(74) *Attorney, Agent, or Firm* — John G. Powell

(57) ABSTRACT

A cleansing composition comprising a detersive surfactant; an aqueous carrier; from about 0.5% to about 30% by weight of the cleansing composition of discrete particles comprising anhydrous particles and an aqueous phase, and wherein said anhydrous particles comprise: one or more fatty amphiphile selected from the group consisting of fatty alcohol, fatty ester, fatty acid, fatty amide and mixtures thereof; of one or more secondary surfactants selected from the group consisting of anionic, nonionic, zwitterionic, cationic or mixtures thereof. Wherein the discrete particle of the cleansing composition has a size from about 500 microns to about 7000 microns, and wherein the cleansing composition has a % transmittance of about 75% or higher.

6 Claims, 3 Drawing Sheets

(51) Int. Cl.

| | | |
|---|---|---|
| *A61K 8/25* | (2006.01) | |
| *A61K 8/26* | (2006.01) | |
| *A61K 8/29* | (2006.01) | |
| *A61K 8/34* | (2006.01) | |
| *A61K 8/36* | (2006.01) | |
| *A61K 8/37* | (2006.01) | |
| *A61K 8/41* | (2006.01) | |
| *A61K 8/42* | (2006.01) | |
| *A61K 8/46* | (2006.01) | |
| *A61K 8/60* | (2006.01) | |
| *A61Q 5/02* | (2006.01) | |
| *A61Q 19/10* | (2006.01) | |

(52) U.S. Cl.
CPC ............. *A61K 8/342* (2013.01); *A61K 8/361* (2013.01); *A61K 8/375* (2013.01); *A61K 8/416* (2013.01); *A61K 8/42* (2013.01); *A61K 8/463* (2013.01); *A61K 8/602* (2013.01); *A61Q 5/02* (2013.01); *A61Q 19/10* (2013.01)

(56) References Cited

U.S. PATENT DOCUMENTS

| | | |
|---|---|---|
| 2,396,278 A | 3/1946 | Otto |
| 2,438,091 A | 3/1948 | Lynch |
| 2,486,921 A | 11/1949 | Byerly |
| 2,486,922 A | 11/1949 | Bruce |
| 2,528,378 A | 10/1950 | McCabe, Jr. |
| 2,658,072 A | 11/1953 | Kosmin |
| 2,694,668 A | 11/1954 | Fricke |
| 2,786,847 A | 3/1957 | Cislak |
| 2,798,053 A | 7/1957 | Brown |
| 2,809,971 A | 10/1957 | Jack |
| 2,826,551 A | 3/1958 | Geen |
| 3,152,046 A | 10/1964 | Maria |
| 3,155,591 A | 11/1964 | Harry |
| 3,236,733 A | 2/1966 | Karsten |
| 3,332,880 A | 7/1967 | Adriaan |
| 3,589,999 A | 6/1971 | Mcrae |
| 3,590,035 A | 6/1971 | Damico |
| 3,655,096 A | 4/1972 | Easter |
| 3,753,196 A | 8/1973 | Kurtz |
| 3,761,418 A | 9/1973 | Parran |
| 3,773,770 A | 11/1973 | Damico |
| 3,852,441 A | 12/1974 | Kooistra |
| 3,929,678 A | 12/1975 | Laughlin et al. |
| 3,940,482 A | 2/1976 | Grand |
| 3,958,581 A | 5/1976 | Abegg |
| 3,959,461 A | 5/1976 | Bailey |
| 3,964,500 A | 6/1976 | Drakoff |
| 4,055,655 A | 10/1977 | Maurer |
| 4,089,945 A | 5/1978 | Brinkman |
| 4,152,416 A | 5/1979 | Marra |
| 4,161,426 A | 7/1979 | Kneer |
| 4,197,865 A | 4/1980 | Jacquet |
| 4,217,914 A | 8/1980 | Jacquet |
| 4,323,683 A | 4/1982 | Bolich, Jr. |
| 4,345,080 A | 8/1982 | Bolich, Jr. |
| 4,364,387 A | 12/1982 | Larkin |
| 4,379,753 A | 4/1983 | Bolich, Jr. |
| 4,381,919 A | 5/1983 | Jacquet |
| 4,387,090 A | 6/1983 | Bolich, Jr. |
| 4,422,853 A | 12/1983 | Jacquet |
| 4,470,982 A | 9/1984 | Winkler |
| 4,507,280 A | 3/1985 | Pohl |
| 4,529,586 A | 7/1985 | De |
| 4,565,647 A | 1/1986 | Llenado |
| 4,604,272 A | 8/1986 | Kratel |
| 4,608,183 A | 8/1986 | Rossmoore |
| 4,663,158 A | 5/1987 | Wolfram |
| 4,666,616 A | 5/1987 | Rossmoore |
| 4,670,430 A | 6/1987 | Imamura |
| 4,686,254 A | 8/1987 | Lochhead |
| 4,704,272 A | 11/1987 | Oh |
| 4,708,863 A | 11/1987 | Bews |
| 4,726,915 A | 2/1988 | Verdicchio |
| 4,788,006 A | 11/1988 | Bolich, Jr. |
| 4,834,767 A | 5/1989 | Helioff |
| 4,885,107 A | 12/1989 | Wetzel |
| 4,898,585 A | 2/1990 | Borsanyi |
| 5,034,218 A | 7/1991 | Duvel |
| 5,057,153 A | 10/1991 | Ruggiero |
| 5,104,646 A | 4/1992 | Bolich, Jr. |
| 5,106,609 A | 4/1992 | Bolich, Jr. |
| 5,106,613 A | 4/1992 | Hartnett |
| 5,114,898 A | 5/1992 | Pinnavaia |
| 5,154,847 A | 10/1992 | Lapetina |
| 5,186,928 A | 2/1993 | Birtwistle |
| 5,202,048 A | 4/1993 | Bartolo |
| 5,227,156 A | 7/1993 | Wiese |
| 5,248,445 A | 9/1993 | Rizvi |
| 5,273,189 A | 12/1993 | Jouillat et al. |
| RE34,584 E | 4/1994 | Grote |
| 5,358,667 A | 10/1994 | Bergmann |
| 5,360,581 A | 11/1994 | Rizvi |
| 5,373,973 A | 12/1994 | Foster |
| 5,462,589 A | 10/1995 | Nicholas |
| 5,466,425 A | 11/1995 | Adams |
| 5,478,501 A | 12/1995 | Rau |
| 5,495,538 A | 2/1996 | Fan |
| 5,518,774 A | 5/1996 | Kappock |
| 5,540,954 A | 7/1996 | Nicholas |
| 5,562,995 A | 10/1996 | Kappock |
| 5,609,862 A | 3/1997 | Chen et al. |
| 5,614,538 A | 3/1997 | Nelson, Jr. |
| 5,674,478 A | 10/1997 | Dodd et al. |
| 5,696,169 A | 12/1997 | Otsu |
| 5,710,114 A | 1/1998 | Pyles |
| 5,726,137 A | 3/1998 | Patel |
| 5,750,122 A | 5/1998 | Evans |
| 5,756,076 A | 5/1998 | Cervantes |
| 5,776,444 A | 7/1998 | Birtwistle et al. |
| 5,785,962 A | 7/1998 | Hinz |
| 5,798,121 A | 8/1998 | Cauwet |
| 5,811,487 A | 9/1998 | Schulz, Jr. et al. |
| 5,836,479 A | 11/1998 | Klima et al. |
| 5,837,661 A | 11/1998 | Evans |
| 5,853,707 A | 12/1998 | Wells |
| 5,854,319 A | 12/1998 | Olenick, Jr. |
| 5,874,476 A | 2/1999 | Hsu |
| 5,876,705 A | 3/1999 | Uchiyama |
| 5,880,076 A | 3/1999 | Vermeer |
| 5,883,154 A | 3/1999 | Kappock |
| 5,885,948 A | 3/1999 | Glenn, Jr. et al. |
| 5,939,059 A | 8/1999 | Franklin |
| 5,939,203 A | 8/1999 | Kappock |
| 5,955,066 A | 9/1999 | Sako |
| 5,965,515 A | 10/1999 | Rau |
| 5,977,036 A | 11/1999 | Guskey |
| 5,997,036 A | 12/1999 | Hamada |
| 5,997,851 A | 12/1999 | Cox |
| 6,017,562 A | 1/2000 | Kaufman |
| 6,034,043 A | 3/2000 | Fujiwara |
| 6,183,766 B1 | 2/2001 | Sine et al. |
| 6,303,109 B1 | 10/2001 | Foerster |
| 6,309,628 B1 | 10/2001 | Ansmann |
| 6,333,040 B1 | 12/2001 | Boyxen |
| RE37,793 E | 7/2002 | Domenico |
| 6,432,420 B2 | 8/2002 | Ellis |
| 6,451,300 B1 | 9/2002 | Dunlop et al. |
| 6,521,238 B1 | 2/2003 | Muller |
| 6,521,239 B1 | 2/2003 | Breton |
| RE38,130 E | 6/2003 | Adams |
| 6,598,762 B2 | 7/2003 | Mckune |
| 6,719,967 B1 | 4/2004 | Brown |
| 6,774,096 B1 | 8/2004 | Paye |
| 6,878,368 B2 | 4/2005 | Ohta et al. |
| 6,908,912 B2 | 6/2005 | Rioux |
| 6,991,799 B2 | 1/2006 | Pham et al. |
| 7,040,311 B2 | 5/2006 | Hochrainer et al. |
| 7,294,611 B2 | 11/2007 | Metrot |
| 7,303,744 B2 * | 12/2007 | Wells .............. A61K 8/042 424/70.28 |

(56) References Cited

U.S. PATENT DOCUMENTS

| | | |
|---|---|---|
| 7,531,497 B2 | 5/2009 | Midha et al. |
| 7,560,125 B2 | 7/2009 | Ananthapadmanabhan et al. |
| 7,776,347 B2 | 8/2010 | Kerschner et al. |
| 8,252,271 B2 | 8/2012 | Singer et al. |
| 8,349,300 B2 | 1/2013 | Wells |
| 8,349,301 B2 | 1/2013 | Wells |
| 8,349,302 B2 | 1/2013 | Johnson |
| 8,361,448 B2 | 1/2013 | Johnson |
| 8,361,449 B2 | 1/2013 | Wells |
| 8,361,450 B2 | 1/2013 | Johnson |
| 8,367,048 B2 | 2/2013 | Wells |
| 8,470,305 B2 | 6/2013 | Johnson |
| 8,635,014 B2 | 1/2014 | Jung |
| 8,653,014 B2 * | 2/2014 | Hilvert .................. A61K 8/817 510/119 |
| 8,655,819 B1 | 2/2014 | Burkard et al. |
| 8,663,612 B2 | 3/2014 | Gamez-Garcia et al. |
| 8,901,062 B2 | 12/2014 | De Meirleir et al. |
| 8,932,569 B2 | 1/2015 | Garrison et al. |
| 8,940,285 B2 | 1/2015 | Leray et al. |
| 8,969,261 B2 | 3/2015 | Talingting Pabalan et al. |
| 9,005,585 B2 | 4/2015 | Deckner et al. |
| 9,138,429 B2 | 9/2015 | Wise et al. |
| 9,381,382 B2 | 7/2016 | Schwartz et al. |
| 9,393,188 B2 | 7/2016 | Deckner et al. |
| 9,539,444 B2 | 1/2017 | Kinoshita |
| 9,587,209 B2 | 3/2017 | De Meirleir et al. |
| 9,724,283 B2 | 8/2017 | Rizk |
| 9,877,909 B2 | 1/2018 | Cetti et al. |
| 10,143,632 B2 | 12/2018 | Dihora et al. |
| 10,226,782 B2 | 3/2019 | Yamaguchi et al. |
| 10,689,183 B2 | 6/2020 | Moretti |
| 10,912,719 B2 | 2/2021 | Gulbin |
| 10,945,935 B2 | 3/2021 | Brown et al. |
| 2001/0047039 A1 | 11/2001 | Mcmanus |
| 2002/0119113 A1 | 8/2002 | Ellis |
| 2002/0131946 A1 | 9/2002 | Pham et al. |
| 2002/0169283 A1 | 11/2002 | Lu |
| 2002/0183300 A1 | 12/2002 | Fliss |
| 2003/0012646 A1 | 1/2003 | Liao |
| 2003/0017126 A1 | 1/2003 | Mahadeshwar |
| 2003/0044471 A1 | 3/2003 | Sakuma |
| 2003/0095938 A1 | 5/2003 | Casero |
| 2003/0119806 A1 | 6/2003 | Lindell |
| 2003/0130145 A1 | 7/2003 | Patel |
| 2003/0138497 A1 | 7/2003 | Sakuma |
| 2003/0171231 A1 | 9/2003 | Shana |
| 2003/0185779 A1 | 10/2003 | Mitsumatsu |
| 2003/0215522 A1 | 11/2003 | Johnson |
| 2003/0223952 A1 | 12/2003 | Wells et al. |
| 2003/0224954 A1 | 12/2003 | Wells et al. |
| 2003/0224955 A1 | 12/2003 | Ribery |
| 2004/0058855 A1 | 3/2004 | Schwartz |
| 2004/0092897 A1 | 5/2004 | Macedo, Jr. |
| 2004/0157754 A1 | 8/2004 | Geary et al. |
| 2004/0167114 A1 | 8/2004 | Fliss |
| 2004/0191331 A1 | 9/2004 | Schwartz |
| 2004/0197294 A1 | 10/2004 | Seipel |
| 2004/0223941 A1 | 11/2004 | Schwartz |
| 2004/0223991 A1 | 11/2004 | Wei et al. |
| 2004/0234471 A1 | 11/2004 | Corbella |
| 2004/0266886 A1 | 12/2004 | Seipel |
| 2005/0031569 A1 | 2/2005 | Seipel |
| 2005/0100570 A1 | 5/2005 | Wei et al. |
| 2005/0112083 A1 | 5/2005 | Wells et al. |
| 2005/0143268 A1 | 6/2005 | Midha |
| 2005/0181067 A1 | 8/2005 | Yokoyama |
| 2005/0196368 A1 | 9/2005 | Laurent et al. |
| 2005/0202984 A1 | 9/2005 | Schwartz |
| 2005/0267258 A1 | 12/2005 | Rajaraman et al. |
| 2006/0024256 A1 | 2/2006 | Wells |
| 2006/0024381 A1 | 2/2006 | Schwartz |
| 2006/0025256 A1 | 2/2006 | Wake |
| 2006/0045861 A1 | 3/2006 | Bejger |
| 2006/0078524 A1 | 4/2006 | Midha et al. |
| 2006/0078527 A1 | 4/2006 | Midha et al. |
| 2006/0079418 A1 | 4/2006 | Wagner et al. |
| 2006/0079419 A1 | 4/2006 | Wagner et al. |
| 2006/0079420 A1 | 4/2006 | Wagner et al. |
| 2006/0079421 A1 | 4/2006 | Wagner et al. |
| 2006/0205631 A1 | 9/2006 | Smerznak et al. |
| 2006/0250658 A1 | 11/2006 | Jurgensen |
| 2006/0251605 A1 | 11/2006 | Belmar |
| 2006/0269501 A1 | 11/2006 | Johnson |
| 2006/0269502 A1 | 11/2006 | Johnson |
| 2007/0095721 A1 | 5/2007 | Davis et al. |
| 2007/0110696 A1 | 5/2007 | Johnson |
| 2007/0110700 A1 | 5/2007 | Wells |
| 2007/0128147 A1 | 6/2007 | Schwartz et al. |
| 2007/0280976 A1 | 12/2007 | Taylor et al. |
| 2008/0039352 A1 | 2/2008 | Wells et al. |
| 2008/0096786 A1 | 4/2008 | Holt et al. |
| 2008/0152611 A1 | 6/2008 | Wells et al. |
| 2008/0187507 A1 | 8/2008 | Johnson |
| 2010/0061952 A1 | 3/2010 | Wells et al. |
| 2010/0226868 A1 | 9/2010 | Gamez-Garcia et al. |
| 2010/0234260 A1 | 9/2010 | Sekine et al. |
| 2010/0322878 A1 | 12/2010 | Stella et al. |
| 2010/0330018 A1 | 12/2010 | Lorant et al. |
| 2011/0053818 A1 | 3/2011 | Chuchotiros et al. |
| 2011/0065624 A1 | 3/2011 | Boutique et al. |
| 2011/0067720 A1 | 3/2011 | Ranade et al. |
| 2011/0070180 A1 | 3/2011 | Ranade et al. |
| 2011/0081392 A1 | 4/2011 | de Arruda et al. |
| 2011/0110991 A1 | 5/2011 | Garrison et al. |
| 2011/0248052 A1 | 10/2011 | Kelly et al. |
| 2012/0148644 A1 | 6/2012 | Popplewell et al. |
| 2012/0164198 A1 * | 6/2012 | Johnson .................. A61K 8/89 424/401 |
| 2012/0308502 A1 | 12/2012 | Wise et al. |
| 2012/0329768 A1 | 12/2012 | Wise et al. |
| 2013/0029894 A1 | 1/2013 | Bettiol et al. |
| 2013/0090279 A1 | 4/2013 | Hilvert et al. |
| 2013/0131188 A1 | 5/2013 | Beckedahl et al. |
| 2013/0143784 A1 | 6/2013 | Rizk |
| 2013/0171216 A1 | 7/2013 | Alden-danforth et al. |
| 2013/0174863 A1 | 7/2013 | Marsh et al. |
| 2013/0243717 A1 | 9/2013 | Catalan et al. |
| 2013/0243835 A1 | 9/2013 | Tanner et al. |
| 2014/0018276 A1 | 1/2014 | Coffindaffer et al. |
| 2014/0099276 A1 | 4/2014 | Yang et al. |
| 2014/0112964 A1 * | 4/2014 | Wu .......................... A61K 8/20 424/401 |
| 2014/0162931 A1 | 6/2014 | De Meirleir et al. |
| 2014/0335041 A1 | 11/2014 | Peffly et al. |
| 2015/0010487 A1 | 1/2015 | Snyder et al. |
| 2015/0011450 A1 | 1/2015 | Carter et al. |
| 2015/0044157 A1 | 2/2015 | Kulkarni et al. |
| 2015/0059795 A1 | 3/2015 | Vatter et al. |
| 2015/0093422 A1 | 4/2015 | Garrison et al. |
| 2015/0102061 A1 | 4/2015 | Larson et al. |
| 2015/0313833 A1 | 11/2015 | Hilvert et al. |
| 2015/0342842 A1 | 12/2015 | Wise et al. |
| 2015/0374609 A1 | 12/2015 | Cetti et al. |
| 2016/0067172 A1 | 3/2016 | Burch et al. |
| 2016/0106663 A1 | 4/2016 | Gulbin |
| 2016/0143827 A1 | 5/2016 | Castan Barberan et al. |
| 2016/0256365 A1 | 9/2016 | Dihora et al. |
| 2017/0216158 A1 | 8/2017 | Deckner et al. |
| 2017/0225183 A1 | 8/2017 | Kelly |
| 2017/0333734 A1 | 11/2017 | Mauer et al. |
| 2017/0367955 A1 | 12/2017 | Brown et al. |
| 2018/0071185 A1 | 3/2018 | Cochran et al. |
| 2018/0098923 A1 | 4/2018 | Hutton, III |
| 2018/0339845 A1 | 11/2018 | Moretti |
| 2019/0201925 A1 | 7/2019 | Toh et al. |
| 2019/0290554 A1 | 9/2019 | Yokogi et al. |
| 2019/0290555 A1 | 9/2019 | Yokogi et al. |
| 2019/0290562 A1 | 9/2019 | Yokogi et al. |
| 2019/0290567 A1 | 9/2019 | Yokogi et al. |
| 2019/0290568 A1 | 9/2019 | Yokogi et al. |
| 2019/0307665 A1 | 10/2019 | Yokogi et al. |
| 2020/0188243 A1 | 6/2020 | Brown et al. |

(56) References Cited

U.S. PATENT DOCUMENTS

| | | |
|---|---|---|
| 2021/0022975 A1 | 1/2021 | Cochran et al. |
| 2021/0045979 A1 | 2/2021 | Dunlop et al. |
| 2021/0121903 A1 | 4/2021 | Yamaguchi et al. |

FOREIGN PATENT DOCUMENTS

| | | |
|---|---|---|
| CN | 1568174 A | 1/2005 |
| CN | 101965175 A | 2/2011 |
| CN | 103458858 A | 12/2013 |
| CN | 105326670 A | 2/2016 |
| CN | 105395373 A | 3/2016 |
| CN | 105326660 B | 4/2018 |
| CN | 105395378 B | 7/2018 |
| EP | 0037318 A1 | 10/1981 |
| EP | 0077630 A1 | 4/1983 |
| EP | 0627216 A2 | 12/1994 |
| EP | 1123693 A2 | 8/2001 |
| EP | 1066024 B1 | 10/2002 |
| EP | 1384467 B1 | 5/2007 |
| EP | 3281619 A1 | 2/2018 |
| EP | 3305273 A1 | 4/2018 |
| FR | 2593801 B1 | 5/1986 |
| FR | 1971709 A1 | 8/2012 |
| GB | 849433 A1 | 9/1960 |
| GB | 1582529 A | 1/1981 |
| GB | 2177108 B | 7/1989 |
| JP | 5209881 A | 8/1977 |
| JP | 06134227 A | 5/1994 |
| JP | H07179887 A | 11/1994 |
| JP | H07118103 A | 5/1995 |
| JP | 07258039 A | 10/1995 |
| JP | 2001181145 A | 7/2001 |
| JP | 2002104940 A | 4/2002 |
| JP | 2003530446 A | 10/2003 |
| JP | 2004262805 A | 9/2004 |
| JP | 2004292387 A | 10/2004 |
| JP | 2004292390 A | 10/2004 |
| JP | 2004307463 A | 11/2004 |
| JP | 2005022983 A | 1/2005 |
| JP | 2005187342 A | 7/2005 |
| JP | 2006063044 A | 3/2006 |
| JP | 2006525232 A | 11/2006 |
| JP | 4016238 B2 | 9/2007 |
| JP | 2007527921 A | 10/2007 |
| JP | 4069228 B2 | 1/2008 |
| JP | 4129645 B2 | 5/2008 |
| JP | 2008524263 A | 7/2008 |
| JP | 2015512248 A | 4/2015 |
| JP | 2016516674 A | 6/2016 |
| WO | 9308787 A1 | 5/1993 |
| WO | 9410973 A1 | 5/1994 |
| WO | 9625913 A1 | 8/1996 |
| WO | 9726854 A1 | 7/1997 |
| WO | 9847372 A1 | 10/1998 |
| WO | 9938489 A1 | 8/1999 |
| WO | 9959540 A1 | 11/1999 |
| WO | 0100149 A1 | 1/2001 |
| WO | 0105932 A1 | 1/2001 |
| WO | 0117492 A1 | 3/2001 |
| WO | 0119946 A1 | 3/2001 |
| WO | 0139735 A1 | 6/2001 |
| WO | 02076422 A1 | 10/2002 |
| WO | 2004020526 A1 | 3/2004 |
| WO | 2004100919 A1 | 11/2004 |
| WO | 2010006866 A1 | 1/2010 |
| WO | 2010034736 A1 | 4/2010 |
| WO | 2010111266 A2 | 9/2010 |
| WO | 2011120799 A1 | 10/2011 |
| WO | 2011134832 A2 | 11/2011 |
| WO | 2012004126 A2 | 1/2012 |
| WO | 2012175677 A2 | 12/2012 |
| WO | 20121756821 A2 | 12/2012 |
| WO | 2013073849 A1 | 5/2013 |
| WO | 2013092719 A1 | 6/2013 |
| WO | 2017088459 A1 | 6/2017 |
| WO | WO2018005453 A1 | 1/2018 |
| WO | WO2018191567 A1 | 10/2018 |
| WO | WO2018191568 A1 | 10/2018 |
| WO | WO2018191569 A1 | 10/2018 |
| WO | WO2018191570 A1 | 10/2018 |
| WO | WO2018191571 A1 | 10/2018 |
| WO | WO2018191572 A1 | 10/2018 |
| WO | WO2018191573 A1 | 10/2018 |
| WO | WO2018191574 A1 | 10/2018 |
| WO | 2021163728 A1 | 8/2021 |

OTHER PUBLICATIONS

"Polyelectrolyte-Micelle—Coacervation—Effect of coacervate on the properties of shampoo", Yoshiko Kiwatari et al., J. Soc. Cosmet. Chem. Japan, vol. 38, No. 3, 2004, pp. 211-219.

Eccleston, G.M., Application of Emulsion Stability Theories to Mobile and Semisolid o/w Emulsions, Cosmetics Magazine, vol. 101, 1986, 18 pages.

Eccleston, G.M., Application of Emulsion Theory to Complex and Real Systems, International Journal of Cosmetic Science, 1985, 18 pages.

Eccleston, G.M., Formulating Cosmetic Emulsions, Cosmetics Magazine, vol. 112, 1997, 2 pages.

Eccleston, G.M., Functions of Mixed Emulsifiers and Emulsifying Waxes in Dermatological Lotions and Creams, Colloids and Surfaces, vol. 123, 1997, 14 pages.

Eccleston, G.M., Microstructural Changes During Storage of Cetostearyl Alcohol/ Polyoxyethylene Alkyl Ether Surfactants, University of Strathclyde, 1988, 20 pages.

Eccleston, G.M., Multiple Phase Oil and Water Emulsions, Journal of Cosmetic Chemists, 1990, 22 pages.

Eccleston, G.M., Structure and Rheology of Semisolid o/w Creams Containing Cetyl Alcohol/Non-ionic Surfactant Mixed Emulsifier and Different Polymers, International Journal of Cosmetic Science, 2004, 7 pages.

Eccleston, G.M., Synchrotron X-ray Investigations into the Lamellar Gel Phase Formed in Creams Prepared with Fatty Alcohols, International Journal of Pharmaceuticals, 2000, 13 pages.

Eccleston, G.M., The Influence of Fatty Alcohols on the Structure and Stability of Creams Preapred with Fatty Alcohols, International Journal of Cosmetic Science, 1982, 9 pages.

All Office Actions, U.S. Appl. No. 16/907,711.
All Office Actions, U.S. Appl. No. 15/635,633.
All Office Actions, U.S. Appl. No. 15/703,046.
All Office Actions, U.S. Appl. No. 15/728,663.
All Office Actions, U.S. Appl. No. 16/713,142.
All Office Actions, U.S. Appl. No. 16/902,629.
All Office Actions, U.S. Appl. No. 17/174,427.
All Office Actions, U.S. Appl. No. 17/326,910.
All Office Actions, U.S. Appl. No. 17/327,972.

Barry & Rowe, The Characterization by Small Angle X-Ray Scattering of a Gel with a Lamellar Structure, International Journal of Pharmaceuticals, 1989, 2 pages.

Barry & Saunders, Kinetics of Structure Build-up in Self Bodied Emulsions Stabalized by Mixed Emulsifiers, Journal of Colloid Science, vol. 41, 1972, 12 pages.

Barry, B.W., Structure and Rheology of Emulsions Stabalized by Mixed Emulsifiers, British Society of Rheology, 1970, 12 pages.

Benton et al, Phase Behavior and Network Formation in a Cationic Surfactant-Fatty Alcohol System, JAOCS, vol. 64, 1987, 12 pages.

Burgess, J.D., Practical Analysis of Complex Coacervate Systems, Journal of Colloid Science, vol. 140, 1990, 10 pages.

CTFA Cosmetic Ingredient Dictionary, 1982, 3rd Edition, The Cosmetic, Toiletry & Fragrance Association, Inc., Washington, DC (book not included).

Database WPI Week 201634Thomson Scientific, London, GB;AN 2016-184949XP002798128,& CN 105 395 373 A (Cuongqing Pellets Coltd) Mar. 16, 2016 (Mar. 16, 2016)abstract, 3 pages.

Database WPI Week 201644Thomson Scientific, London, GB;AN 2016-14284BXP002798127,& CN 105 326 660 A (Chongqjng Pellets Colid) Feb. 17, 2016 (Feb. 17, 2016)abstract, 3 pages.

(56) References Cited

OTHER PUBLICATIONS

Encyclopedia of Polymer Science and Engineering, John Wiley & Sons, vol. 15, 1989 (book not included).
Griffin, W.C., Calculation of HLB Values of Non-Ionic Surfactants, Journal of the Society of Cosmetic Chemists; 1954. vol. 5, pp. 249-235.
INCi: Ricinus Communis (Castor) Seed Oil, 3 pages.
Korhonen et al, Rheological Properties of Three Component Creams Containing Sorbitan Monoesters as Surfactants, International Journal of Pharmaceuticals, 2002, 2 pages.
Louden et al, A Preliminary Examination of the Structure of Gels and Emulsions Containing Cetostearyl Alcohol, International Journal of Pharmaceuticals, 1985, 2 pages.
McCutcheon, Emulsifiers and Detergents, MC Pub Company, 1989 (book not included).
Meirleir Niels De et al., "The rheological properties of hydrogenated castor oil crystals", Colloid & Polymer Science, Springer Verlag, Heidelberg, DE, vol. 292, No. 10, Jun. 12, 2014, pp. 2539-2547.
Momentive SFE839 product brochure, https://www.momentive.com/products/showtechnicaldatasheet.aspx?id=14443, 4 pagesavailable Sep. 2008; accessed Jul. 17, 2015.
Noll, W., Chemistry and Technology of Silicones, Academic Press, 1968 (book not included).
Patel et al, Properties of Cetrimide / Cetostearyl Alcohol Ternary Gels; Preparation Effects, International Journal of Pharmaceuticals, 1985, 2 pages.
PCT International Search Report and Written Opinion for PCT/US2019/035485 dated Sep. 23, 2019, 12 pages.
Savic et al, Colloidal Microstructure of Binary Systems and Model Creams Stablized with an Alkylpolyglucoside Emulsifier, Colloid Polymer Science, vol. 283, 2004, 13 pages.
Saxton, C., Antiplaque Effects and Mode of Action of a Combination of Zinc Citrate and a Nonionic Antimicrobial Agent, Scandinavian Journal, vol. 96, 1988, 7 pages.
Suzuki et al, Secondary Droplet Emulsion: Mechanism & Effects of Liquid Crystal Formation in o/w Emulsion, Journal of Dispersion Science, 1984, 24 pages.
U.S. Appl. No. 17/174,427, filed Feb. 12, 2021, to Stefano Bartolucci et al.
U.S. Appl. No. 17/326,910, filed May 21, 2021, to Howard David Hutton.
U.S. Appl. No. 17/327,972, filed May 24, 2021, to Howard David Hutton.
Van Cutsem, Journal of the American Academy of Dermatology, XP-002288119, 1998, 2 pages.
Van Oss, C.J., Coacervation, Complex Coacervation and Flocculation, Journal of Dispersion Science, vol. 9, 1989, 14 pages.
Yoon et al, A Study of Gel Structure in the Nonionic Surfactant / Cetostearyl Alcohol / Water Ternary Systems by Differential Scanning Calorimeter, Journal of Dispersion Science, 1999, 20 pages.
De Meirleir et al. "Journal of Crystal Growth" 2013; 383: 51-56. (Year: 2013).
All Office Actions; U.S. Appl. No. 17/184,814, filed Feb. 25, 2021.
All Office Actions; U.S. Appl. No. 17/174,713, filed Feb. 12, 2021.
U.S. Appl. No. 17/184,814, filed Feb. 25, 2021, to Mark Anthony Brown et al.
U.S. Appl. No. 17/174,713, filed Feb. 12, 2021, to Mark Anthony Brown et al.

* cited by examiner

CLEAR CLEANSING COMPOSITION

FIELD OF THE INVENTION

A clear cleansing composition comprising discrete particles which deliver benefits.

BACKGROUND OF THE INVENTION

Some consumers prefer clear cleansing compositions. Traditionally, clear cleansing compositions, such as shampoos, clean very effectively but often lack adequate conditioning benefits; as the conditioning actives traditionally deliver an opaque appearance to the cleansing products. Therefore, it would be beneficial to introduce in the market clear cleansing compositions, such as shampoos, that provide conditioning hair benefits that are offered today only by conventional opaque cleansing products.

Current cleansing compositions, such as shampoos that use large particle silicones, or those that contain insoluble levels of fatty amphiphile (higher than about 0.5%) added as conventional dispersed phase gel network, are necessarily opaque due to the scale size of the dispersed gel network phase therein or silicone particles, which size can be as large as 150 micrometers.

Therefore, a need exists to provide a clear cleansing composition that provides conditioning benefits that are offered today only by conventional opaque shampoos. A need also exists for clear cleansing compositions to contain benefit agents that are opaque or are typically incompatible with the other materials included in a cleansing composition.

SUMMARY OF THE INVENTION

A cleansing composition comprising a detersive surfactant; an aqueous carrier; from about 0.5% to about 30% by weight of the cleansing composition of discrete particles comprising anhydrous particles and an aqueous phase, and wherein said anhydrous particles comprise: one or more fatty amphiphile selected from the group consisting of fatty alcohol, fatty ester, fatty acid, fatty amide and mixtures thereof; of one or more secondary surfactants selected from the group consisting of anionic, nonionic, zwitterionic, cationic or mixtures thereof; wherein the discrete particle has a size from about 200 microns to about 15000 microns, wherein the cleansing composition has a % transmittance of about 75% or higher.

DETAILED DESCRIPTION OF THE INVENTION

Figure 1:
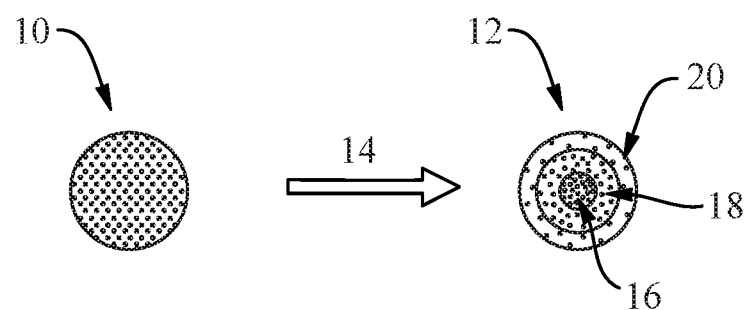
FIG. 1 is a diagram showing particle hydration.

While the specification concludes with claims particularly pointing out and distinctly claiming the invention, it is believed that the present invention will be better understood from the following description.

Herein, "comprising" means that other steps and other ingredients which do not affect the end result can be added. This term encompasses the terms "consisting of" and "consisting essentially of".

All percentages, parts and ratios are based upon the total weight of the compositions of the present invention, unless otherwise specified. All such weights as they pertain to listed ingredients are based on the active level and, therefore, do not include solvents or by-products that may be included in commercially available materials, unless otherwise specified. The term "weight percent" may be denoted as "wt. %" herein.

As used herein, "molecular weight" or "Molecular weight" refers to the weight average molecular weight expressed as grams/mole, unless otherwise stated. Molecular weight is measured using industry standard method, gel permeation chromatography ("GPC").

The term "polymer" as used herein shall include materials compositions to provide conditioning whether made by polymerization of one type of monomer or benefits. As used herein, the term "gel network" refers to a lamellar or vesicular solid crystalline phase which comprises at least one fatty amphiphile and at least one secondary surfactant and water or other suitable solvents, where the fatty alcohol and surfactant within this phase are arranged in multi-lamellar vesicles and/or lamellar sheets. The term "solid crystalline", as used herein, refers to the structure of the lamellar or vesicular phase which forms at a temperature below the melt transition temperature (i.e., the chain melt temperature) of the layer in the gel network, the melt transition temperature being at least about 27° C. The melt transition temperature may be measured by differential scanning calorimetry.

The term "charge density", as used herein, refers to the ratio of the number of positive charges on a polymer to the molecular weight of said polymer.

The compositions and methods/processes of the present invention can comprise, consist of, and consist essentially of the essential elements and limitations of the invention described herein, as well as any of the additional or optional ingredients, components, steps, or limitations described herein.

The term cleansing composition or shampoo as used herein means a composition that is used to clean hair or skin, including scalp, face and body.

The term "suitable for application to human hair" as used herein means that the compositions or components thereof so described are suitable for use in contact with human hair and the scalp and skin without undue toxicity, incompatibility, instability, allergic response, and the like.

The term "water soluble" as used herein means that the material is soluble in water in the composition. In general, the material should be soluble at 25° C. at a concentration of 0.1% by weight of the water solvent, alternatively at 1%, alternatively at 5%, and alternatively at 15%.

The term "discrete particles" means an anhydrous particle swollen in the presence of an aqueous phase (e.g. when the anhydrous particle is added to the detersive surfactant and aqueous phase to form a shampoo product).

The term "anhydrous particles" as used herein means particles prepared by the co-melting and mixing of one or more surfactants and one or more fatty amphiphiles followed by cooling to solidify. The concentration of water in the anhydrous particle generally ranges from about 0% to about 30%, alternatively from about 0% to about 20%, alternatively from about 0% to about 15% by weight of the anhydrous particle. The size of the anhydrous particles in the cleansing composition ranges from about 200 μm to about 10,000 μm. The scale size of the discrete particles in the cleansing composition ranges from about 200 microns to about 15,000 microns, alternatively from about 500 μm to about 7000 μm. The scale size of the discrete particles in the cleansing composition can also range from about 1000 μm to about 5000 μm. As measured by conventional techniques, visually via ruler, light microscopy etc.

The term "solid" as used herein means that the anhydrous particle at ambient temperature does not conform to the shape of the container in which the particle is held.

The term "swollen" as used herein refers to the condition of the discrete particle in the cleansing composition, which particle has absorbed a sufficient quantity of aqueous solvent such that said particle either 1) has a compression of from about 0.5 gram-force units to about 50 gram-force units as determined using the Kawabata KES-FB3-Auto Compression Tester, wherein said particle has a "semi-hydrated gel phase", or 2) has reached maximum equilibrium as a "hydrated gel phase", which phase, having a compression force<0.5 gram-force units, is too soft to measure its compression using the Kawabata KES-FB3-Auto Compression Tester.

The term "unhydrated solid phase" as used herein refers to the portion of the discrete particle in the cleansing composition that has absorbed the least amount of water and which phase has a compression force greater than about 50 gram-force units as determined using the Kawabata KES-FB3-Auto Compression Tester.

As used herein, "clear" composition means permitting a substantial amount of visible light to transmit through an object, for example, the cleansing composition. Suitable light transmittance can be determined using a UV/Vis spectrometer. As used herein, suitable light transmittance can mean, about 60% or more light having a wavelength of 400 nm can transmit through a standard sample, alternatively, about 70% or more light having a wavelength of 400 nm can transmit through a standard sample, alternatively, about 75% or more light having a wavelength of 400 nm can transmit through a standard sample, alternatively, about 80% or more light having a wavelength of 400 nm can transmit through a standard sample; alternatively from about 75% to about 99% light having a wavelength of 400 nm can transmit through a standard sample. The suitable light transmittance can be from about 60%, about 70%, about 75%, about 80% to about 99%, about 95%, about 90% having a wavelength of 400 nm can transmit through a standard sample.

Cleansing Composition

The cleansing composition comprises a detersive surfactant, an aqueous carrier and discrete particles. The discrete particle is an anhydrous particle swollen in the presence of an aqueous phase (e.g. when the anhydrous particle is added to the detersive surfactant and aqueous phase to form a shampoo product). The anhydrous particle comprises a fatty amphiphile, at least one secondary surfactant and a low level of an aqueous phase. The low level of aqueous phase used during the formation of the anhydrous particles is from about 0% by weight of the anhydrous particle to about 30% by weight of the anhydrous particle. The shampoo composition can be substantially clear, having a % transmittance of 75% or greater, alternatively from about 75% to about 99%.

Discrete Particles

The cleansing compositions comprise discrete particles that comprise anhydrous particles and an aqueous phase. The anhydrous particles are prepared by co-melting one or more fatty amphiphile and one or more secondary surfactants and then cooled to solidify. Various methodologies can be used to control the particle size of such anhydrous particles. The anhydrous particles are then added into an aqueous phase that contains detersive surfactant. This results in the swelling of such particles transforming them into discrete particles. The discrete particle can be a gel network.

The size of the discrete particles in the cleansing composition ranges from about 200 μm to about 15,000 μm. Alternatively, the scale size of the discrete particles in the cleansing composition ranges from about 500 μm to about 7000 μm. Alternatively, the scale size of the discrete particles in the cleansing composition ranges from about 1000 μm to about 5000 μm. As measured by conventional techniques, visually via ruler, light microscopy etc.

1. Fatty Amphiphile

The anhydrous particles comprise at least one fatty amphiphile. As used herein, "fatty amphiphile" refers to a compound having a hydrophobic tail group and a hydrophilic head group which does not make the compound water soluble, wherein the compound also has a net neutral charge at the pH of the cleansing composition.

The fatty amphiphile may be characterized as a compound having a Hydrophilic-Lipophilic Balance ("HLB") of 6 or less. The HLB, as used herein, is the standard HLB according to Griffin, J. Soc. Cosm. Chem., vol. 5, 249 (1954).

Suitable fatty amphiphiles, or suitable mixtures of two or more fatty amphiphiles, have a melting point of at least about 27° C. The melting point, as used herein, may be measured by a standard melting point method as described in U.S. Pharmacopeia, USP-NF General Chapter <741>"Melting range or temperature". The melting point of a mixture of two or more materials is determined by mixing the two or more materials at a temperature above the respective melt points and then allowing the mixture to cool. If the resulting composite is a homogeneous solid below about 27° C., then the mixture has a suitable melting point. A mixture of two or more fatty amphiphiles, wherein the mixture comprises at least one fatty amphiphile having an individual melting point of less than about 27° C., still is suitable for use provided that the composite melting point of the mixture is at least about 27° C.

Suitable fatty amphiphiles have a hydrophobic tail group. This hydrophobic tail group may be an alkyl, alkenyl (containing up to 3 double bonds), alkyl aromatic, or branched alkyl group with a length of from about 12 to about 70 carbon atoms, and from about 16 to about 60 carbon atoms, and from about 16 to about 50 carbon atoms, and from about 16 to about 40 carbon atoms, and from about 16 to about 22 carbon atoms, and from about 18 to 22 carbon atoms. Non-limiting examples of alkyl, alkenyl, or branched alkyl groups suitable for the fatty amphiphiles include lauryl, tridecyl, myristyl, pentadecyl, cetyl, heptadecyl, stearyl, arachidyl, behenyl, undecylenyl, palmitoleyl, oleyl, palmoleyl, linoleyl, linolenyl, arahchidonyl, elaidyl, elaeostearyl, erucyl, isolauryl, isotridecyl, isomyristal, isopentadecyl, petroselinyl, isocetyl, isoheptadecyl, isostearyl, isoarachidyl, isobehnyl, gadoleyl, brassidyl, and technical-grade mixture thereof.

Suitable fatty amphiphiles also have a hydrophilic head group which does not make the compound water soluble, such as in compounds having an HLB of 6 or less. Non-limiting examples of classes of compounds having such a hydrophilic head group include fatty alcohols, alkoxylated fatty alcohols, fatty phenols, alkoxylated fatty phenols, fatty amides, alkyoxylated fatty amides, fatty amines, fatty alkylamidoalkylamines, fatty alkyoxyalted amines, fatty carbamates, fatty amine oxides, fatty acids, alkoxylated fatty acids, fatty diesters, fatty sorbitan esters, fatty sugar esters, methyl glucoside esters, fatty glycol esters, mono, di & tri glycerides, polyglycerine fatty esters, alkyl glyceryl ethers, propylene glycol fatty acid esters, cholesterol, ceramides, fatty silicone waxes, fatty glucose amides, fatty phosphate esters, and phospholipids. For additional discussion of fatty amphiphiles which are suitable for use, see U.S. 2006/0024256 A1.

To form the anhydrous particles individual fatty amphiphile compounds or combinations of two or more different fatty amphiphile compounds may be selected.

The discrete particle, is added into a shampoo base to result in a shampoo composition. Therefore, the shampoo compositions can comprise fatty amphiphile in an amount from about 0.05% to about 20%, alternatively from about 0.5% to about 10%, and alternatively from about 1% to about 8%, by weight of the shampoo composition.

The discrete particle, when hydrated, can form a gel network in the shampoo composition. The weight ratio of the fatty amphiphile to the secondary surfactant in the gel network component is greater than about 1:9, alternatively greater than about 1:5 to about 100:1, alternatively greater than about 1:2 to about 50:1, and alternatively greater than about 1:1 to about 1.0:1.

2. Secondary Surfactant Used for the Preparation of the Anhydrous Particles

The anhydrous particles can also comprise one or more secondary surfactant. This secondary surfactant which is combined with the fatty amphiphile to form the anhydrous particle are co-melted and mixed and then cooled to produce the anhydrous particles. The secondary surfactant that is used for the preparation of the anhydrous particle is separate from and in addition to the detersive surfactant component of the cleansing composition. However, this secondary surfactant may be the same or different type of surfactant or surfactants as that or those selected for the detersive surfactant component described above.

The cleansing compositions comprise secondary surfactant as part of the anhydrous particles in an amount from about 0.01% to about 50%, alternatively from about 0.1% to about 10%, and alternatively from about 0.3% to about 5%, by weight of the cleansing composition.

Suitable secondary surfactants include anionic, zwitterionic, amphoteric, cationic, and nonionic surfactants. Alternatively, the secondary surfactant is selected from anionic, cationic, and nonionic surfactants, and mixtures thereof. For additional discussion of surfactants which are suitable for use. see U.S. 2006/0024256 A1.

Additionally, certain secondary surfactants which have a hydrophobic tail group with a chain length of from about 16 to about 22 carbon atoms may be selected to contribute to obtaining a melt transition temperature of at least about 38° C. for the resulting anhydrous particles. For such secondary surfactants, the hydrophobic tail group may be alkyl, alkenyl (containing up to 3 double bonds), alkyl aromatic, or branched alkyl.

Mixtures of more than one surfactant of the above specified types may be used for the secondary surfactant.

The discrete particle may also comprise a secondary surfactant. As used herein, "secondary surfactant" refers to one or more surfactants which are combined with the fatty amphiphile and water. The secondary surfactant is separate from and in addition to the detersive surfactant component of the cleansing composition. However, the secondary surfactant may be the same or different type of surfactant or surfactants as that or those selected for the detersive surfactant component described above.

3. Water or Suitable Solvents

The anhydrous particle may further comprise from about 0 wt % to about 30 wt %, alternatively from about 1 wt % to about 20 wt %, alternatively from about 0 wt % to about 5 wt %, alternatively from about 1 wt % to about 10 wt % of water or a suitable solvent, by weight of the anhydrous particle. As used herein, the term "suitable solvent" refers to any solvent which can be used in the place of or in combination with water.

Cleansing Composition Base

The discrete particle is then added into a cleansing composition base (such as a shampoo base). The shampoo base can comprise a cationic deposition polymer, a surfactant, a co-surfactant, an aqueous carrier and additional components such as silicones.

The anhydrous particles when added to the cleansing composition base (which comprise an aqueous phase) become discrete particles. The discrete particles then swell in the aqueous phase. The aqueous phase comprises water and/or suitable solvents. As used herein, the term "suitable solvent" refers to any solvent which can be used in the place of or in combination with water.

Cationic Deposition Polymer

The cleansing compositions may include a cationic deposition polymer. The concentration of the cationic deposition polymer in the cleansing composition can be from about 0.05% to about 5%, alternatively from about 0.075% to about 2.5%, alternatively from about 0.1% to about 1.0%, and alternatively from about 0.5% to about 1.0% by weight of the cleansing composition.

Suitable cationic deposition polymers may have cationic charge densities of at least about 0.4 meq/g, alternatively at least about 0.7 meq/g, alternatively at least about 1.2 meq/g, alternatively at least about 1.5 meq/g, alternatively less than about 7 meq/g, and alternatively less than about 5 meq/g, at the pH of intended use of the composition. The pH will generally range from about pH 3 to about pH 9, alternatively between about pH 4 and about pH 8. The "cationic charge density" of a polymer, as that term is used herein, refers to the ratio of the number of positive charges on the polymer to the molecular weight of the polymer. The weight average molecular weight of such suitable cationic polymers will generally be between about 10,000 and 10 million, alternatively between about 50,000 and about 5 million, and alternatively between about 100,000 and about 3 million.

Suitable cationic polymers for use in the composition include polysaccharide polymers, such as cationic cellulose derivatives and cationic starch derivatives, such as salts of hydroxyethyl cellulose reacted with trimethyl ammonium substituted epoxide. Other suitable cationic polymers include cationic guar gum derivatives, such as guar hydroxypropyltrimonium chloride. Further suitable cationic polymers include galactomannan polymer derivatives having a mannose to galactose ratio of greater than 2:1 on a monomer to monomer basis, such as cassia gum hydroxypropyltrimonium chloride. Particularly suitable cationic deposition polymers include guar hydroxypropyltrimonium chloride.

The cationic guar polymer may be formed from quaternary ammonium compounds. The quaternary ammonium compounds for forming the cationic guar polymer conform to the general formula 1:

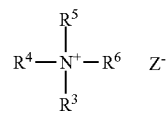

wherein where R3, R4 and R5 are methyl or ethyl groups; R6 is either an epoxyalkyl group of the general formula 2:

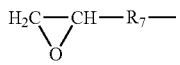

or R6 is a halohydrin group of the general formula 3:

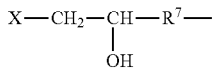

wherein R7 is a C1 to C3 alkylene; X is chlorine or bromine, and Z is an anion such as Cl—, Br—, I— or HSO4-.

The cationic guar polymer can conform to the general formula 4:

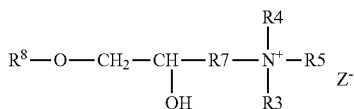

wherein R8 is guar gum; and wherein R4, R5, R6 and R7 are as defined above; and wherein Z is a halogen. The cationic guar polymer can conform to Formula 5:

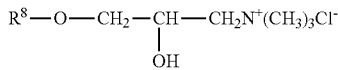

Suitable cationic guar polymers include cationic guar gum derivatives, such as guar hydroxypropyltrimonium chloride. The cationic guar polymer is a guar hydroxypropyltrimonium chloride. Specific examples of guar hydroxypropyltrimonium chlorides include the Jaguar® series commercially available from Rhone-Poulenc Incorporated, for example Jaguar® C-17, which has a cationic charge density of about 0.6 meq/g and a M.Wt. of about 2.2 million g/mol and is available from Rhodia Company. Jaguar® C 13S which has a M.Wt. of 2.2 million g/mol and a cationic charge density of about 0.8 meq/g (available from Rhodia Company). N-Hance 3196, which has a charge density of about 0.7 and a M. Wt. Of about 1,100,000 g/mole and is available from ASI. BF-13, which is a borate (boron) free guar of charge density of about 1.1 meq/g and M. W.t of about 800,000 and BF-17, which is a borate (boron) free guar of charge density of about 1.7 meq/g and M. W.t of about 800,000 both available from ASI.

A combination of cationic polymers can improve the conditioning and lather of the cleansing composition. Using a cationic polymer with a charge density of from about 0.4 meq/g to about 0.8 meq/g, alternatively about 0.7 meq/g in combination with a cationic polymer having a molecular weight greater than about 1,000,000 can result in a cleansing composition with both lather stability and creaminess.

The cleansing composition can comprise a combination of cationic guar and cationic polysaccharide deposition polymers wherein the respective weight ratio of guar to polysaccharide deposition polymers is greater than 2:1, alternatively wherein the weight ratio of guar to polysaccharide deposition polymers is greater than 3:1, and alternatively wherein the weight ratio of guar to polysaccharide deposition polymers is greater than 4:1.

The cleansing composition can comprise a combination of cationic guar polymers only, wherein one cationic guar has a charge density of about 1.7 meq/ g and another cationic guar has a molecular weight of about 1,100,000 g/mole.

The cleansing composition can comprise a mixture of 3196 guar and BF-17 cationic guar, wherein the weight ratio of these two cationic deposition polymers is about 5:1, alternatively about 2:1, alternatively about 1:1, still alternatively about 1:2, and alternatively about 2:5 of 3196 to BF-17 respectively.

The cleansing composition can comprise polyquaternium-6, i.e., homopolymer of diallyldimethylammonium chloride.

The polyquaternium-6 can be included in the composition at a level by weight of from about 0.01% to about 5%, alternatively from about 0.03% to about 1%, alternatively from about 0.05% to about 0.5%, and alternatively from about 0.05% to about 0.3%, by weight of the cleansing composition.

The polyquaternium-6 useful herein has a cationic charge density of, from about 3.5 meq/g, alternatively from about 4.5 meq/g, alternatively from about 5.5 meq/g, and alternatively to about 13 meq/g, alternatively to about 10 meq/g, alternatively to about 7.0 meq/g.

The polyquaternium-6 useful herein has a molecular weight of, from about 800 g/mol or more, alternatively from about 1,000 g/mol or more, alternatively from about 1,200 g/mol or more in view of providing improved deposition of metal pyrithione. The molecular weight is also from about 1,000,000 g/mol, alternatively from about 500,000 g/mol, alternatively from about 100,000 g/mol to about 50,000 g/mol.

Commercially available examples of polyquaternium-6 polymer include, for example, that having a tradename Merquat 100 available from Lubrizol, which has a cationic charge density of about 6.19 meq/g, molecular weight of about 150,000 g/mol, and that having a tradename Merquat 106 available from Lubrizol, which has a cationic charge density of about 6.19 meq/g, molecular weight of about 15,000 g/mol.

Detersive Surfactant

The cleansing composition comprises one or more detersive surfactants in the cleansing base. The detersive surfactant component is included in cleansing compositions to provide cleansing performance. The detersive surfactant may be selected from anionic detersive surfactant, zwitterionic, or amphoteric detersive surfactant, or a combination thereof. Such surfactants should be physically and chemically compatible with the components described herein, or should not otherwise unduly impair product stability, aesthetics or performance. Particularly suitable herein is sodium laureth-n-sulfate, wherein n=1 ("SLE1S"). SLE1S enables more efficient lathering and cleaning when compared to higher mole ethoxylate equivalents, especially in a cleansing composition that contains high levels of conditioning actives.

Suitable anionic detersive surfactants include those which are known for use in hair care or other personal care cleansing compositions. The anionic detersive surfactant may be a combination of sodium lauryl sulfate and sodium laureth-n sulfate. The concentration of the anionic surfactant in the composition should be sufficient to provide the desired cleaning and lather performance, and generally range from about 5% to about 50%, alternatively from about 8% to about 30%, alternatively from about 9% to about 25%, and alternatively from about 10% to about 17%, by weight of the composition.

Suitable zwitterionic or amphoteric detersive surfactants include those which are known for use in hair care or other personal cleansing compositions. Concentration of such amphoteric detersive surfactants range from about 0.5% to about 20%, alternatively from about 1% to about 10%. Non-limiting examples of suitable zwitterionic or amphoteric surfactants are described in U.S. Pat. Nos. 5,104,646 and 5,106,609.

Additional anionic surfactants suitable for use herein include alkyl and alkyl ether sulfates of the formula $ROSO_3M$ and $RO(C_2H_4O)_xSO_3M$, wherein R is alkyl or alkenyl of from about 8 to about 18 carbon atoms, x is 1 to 10, and M is a water-soluble cation such as ammonium, sodium, potassium, and triethanolamine cation or salts of the divalent magnesium ion with two anionic surfactant anions. The alkyl ether sulfates may be made as condensation products of ethylene oxide and monohydric alcohols having from about 8 to about 24 carbon atoms. The alcohols can be derived from fats such as coconut oil, palm oil, palm kernel oil, or tallow, or can be synthetic.

Other suitable anionic surfactants include water-soluble salts of the organic, sulfonic acids of the general formula $[R^1—SO_3M]$. $R^1$ being a straight chain aliphatic hydrocarbon radical having from 13 to 17 carbon atoms, alternatively from 13 to 15 carbon atoms. M is a water soluble cation such as ammonium, sodium, potassium, and triethanolamine cation or salts of the divalent magnesium ion with two anionic surfactant anions. These materials are produced by the reaction of $SO_2$ and $O_2$ with suitable chain length normal paraffins ($C_{14}$-$C_{17}$) and are sold commercially as sodium paraffin sulfonates.

Examples of additional anionic surfactants suitable for use include, but are not limited to, ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, monoethanolamine cocoyl sulfate, sodium trideceth sulfate, sodium tridecyl sulfate, sodium methyl lauroyl taurate, sodium methyl cocoyl taurate, sodium lauroyl isethionate, sodium cocoyl isethionate, sodium laurethsulfosuccinate, sodium laurylsulfosuccinate, sodium tridecyl benzene sulfonate, sodium dodecyl benzene sulfonate, and mixtures thereof.

The cleansing composition may further comprise additional surfactants for use in combination with the anionic detersive surfactant component described herein. Suitable additional surfactants include cationic and nonionic surfactants.

Non-limiting examples of other anionic, zwitterionic, amphoteric, cationic, nonionic, or optional additional surfactants suitable for use in the compositions are described in McCutcheon's, Emulsifiers and Detergents, 1989 Annual, published by M. C. Publishing Co., and U.S. Pat. Nos. 3,929,678; 2,658,072; 2,438,091; and 2,528,378.

The one or more additional anionic surfactants may be selected from the group consisting of isethionates, sarcosinates, sulfonates, sulfosuccinates, sulfoacetates, acyl glycinates, acyl alaninates, acyl glutamates, lactates, lactylates, glucose carboxylates, amphoacetates, taurates, phosphate esters, and mixtures thereof. In that case, alkyl is defined as a saturated or unsaturated, straight or branched alkyl chain with 7 to 17 carbon atoms, alternatively with 9 to 13 carbon atoms. In that case, acyl is defined as of formula R—C(O)—, wherein R is a saturated or unsaturated, straight or branched alkyl chain with 7 to 17 carbon atoms, alternatively with 9 to 13 carbon atoms.

Suitable isethionate surfactants can include the reaction product of fatty acids esterified with isethionic acid and neutralized with sodium hydroxide. Suitable fatty acids for isethionate surfactants can be derived from coconut oil or palm kernel oil including amides of methyl tauride. Non-limiting examples of isethionates can be selected from the group consisting of sodium lauroyl methyl isethionate, sodium cocoyl isethionate, ammonium cocoyl isethionate, sodium hydrogenated cocoyl methyl isethionate, sodium lauroyl isethionate, sodium cocoyl methyl isethionate, sodium myristoyl isethionate, sodium oleoyl isethionate, sodium oleyl methyl isethionate, sodium palm kerneloyl isethionate, sodium stearoyl methyl isethionate, and mixtures thereof.

Non-limiting examples of sarcosinates can be selected from the group consisting of sodium lauroyl sarcosinate, sodium cocoyl sarcosinate, sodium myristoyl sarcosinate, TEA-cocoyl sarcosinate, ammonium cocoyl sarcosinate, ammonium lauroyl sarcosinate, dimer dilinoleyl bis-lauroyl-glutamate/lauroyls arcosinate, di sodium lauroamphodiacetate, lauroyl sarcosinate, isopropyl lauroyl sarcosinate, potassium cocoyl sarcosinate, potassium lauroyl sarcosinate, sodium cocoyl sarcosinate, sodium lauroyl sarcosinate, sodium myristoyl sarcosinate, sodium oleoyl sarcosinate, sodium palmitoyl sarcosinate, TEA-cocoyl sarcosinate, TEA-lauroyl sarcosinate, TEA-oleoyl sarcosinate, TEA-palm kernel sarcosinate, and combinations thereof.

Non-limiting examples of sulfosuccinate surfactants can include disodium N-octadecyl sulfosuccinate, disodium lauryl sulfosuccinate, diammonium lauryl sulfosuccinate, sodium lauryl sulfosuccinate, disodium laureth sulfosuccinate, tetrasodium N-(1,2-dicarboxyethyl)-N-octadecyl sulfosuccinnate, diamyl ester of sodium sulfosuccinic acid, dihexyl ester of sodium sulfosuccinic acid, dioctyl esters of sodium sulfosuccinic acid, and combinations thereof.

Non-limiting examples of sulfoacetates can include sodium lauryl sulfoacetate, ammonium lauryl sulfoacetate and combination thereof.

Non-limiting examples of acyl glycinates can include sodium cocoyl glycinate, sodium lauroyl glycinate and combination thereof.

Non-limiting example of acyl alaninates can include sodium cocoyl alaninate, sodium lauroyl alaninate, sodium N-dodecanoyl-1-alaninate and combinations thereof.

Non-limiting examples of acyl glutamates can be selected from the group consisting of sodium cocoyl glutamate, disodium cocoyl glutamate, ammonium cocoyl glutamate, diammonium cocoyl glutamate, sodium lauroyl glutamate, disodium lauroyl glutamate, sodium cocoyl hydrolyzed wheat protein glutamate, disodium cocoyl hydrolyzed wheat protein glutamate, potassium cocoyl glutamate, dipotassium cocoyl glutamate, potassium lauroyl glutamate, dipotassium lauroyl glutamate, potassium cocoyl hydrolyzed wheat protein glutamate, dipotassium cocoyl hydrolyzed wheat protein glutamate, sodium capryloyl glutamate, disodium capryloyl glutamate, potassium capryloyl glutamate, dipotassium capryloyl glutamate, sodium undecylenoyl glutamate, disodium undecylenoyl glutamate, potassium undecylenoyl glutamate, dipotassium undecylenoyl glutamate, disodium hydrogenated tallow glutamate, sodium stearoyl glutamate, disodium stearoyl glutamate, potassium stearoyl glutamate, dipotassium stearoyl glutamate, sodium myristoyl glutamate, disodium myristoyl glutamate, potassium myristoyl glutamate, dipotassium myristoyl glutamate, sodium cocoyl/hydrogenated tallow glutamate, sodium cocoyl/palmoyl/sunfloweroyl glutamate, sodium hydrogenated tallowoyl glutamate, sodium olivoyl glutamate, disodium olivoyl glutamate, sodium palmoyl glutamate, disodium palmoyl glutamate, TEA-cocoyl glutamate, TEA-hydrogenated tallowoyl glutamate, TEA-lauroyl glutamate, and mixtures thereof.

Non-limiting examples of acyl glycinates can include sodium cocoyl glycinate, sodium lauroyl glycinate and combination thereof.

Non-limiting example of lactates can include sodium lactate.

Non-limiting examples of lactylates can include sodium lauroyl lactylate, sodium cocoyl lactylate and combination thereof.

Non-limiting examples of glucose carboxylates can include sodium lauryl glucoside carboxylate, sodium cocoyl glucoside carboxylate and combinations thereof.

Non-limiting examples of alkylamphoacetates can include sodium cocoyl amphoacetate, sodium lauroyl amphoacetate and combination thereof.

Non-limiting examples of acyl taurates can include sodium methyl cocoyl taurate, sodium methyl lauroyl taurate, sodium methyl oleoyl taurate and combination thereof.

Co-Surfactant

Co-surfactants are materials which are combined with the undecyl sulfate surfactant and optionally anionic surfactants to enhance lather volume and/or to modify lather texture. Typically these materials can be selected from a variety of families of structures including, but not limited to, amphoteric, zwitterionic, cationic, and nonionic. They are typically used with anionic surfactants in a weight ratio of 1:20 to 1:4, and alternatively in the 1:12 to 1:7 weight ratio.

The cleansing composition may comprise from about 0.5 wt % to about 10 wt %, alternatively from about 0.5 wt % to about 5 wt %, alternatively from about 0.5 wt % to about 3 wt %, alternatively from about 0.5 wt % to about 2 wt %, and alternatively from about 0.5 wt % to about 1.75 wt % by weight of the composition of at least one suitable co-surfactant. The co-surfactant may serve to produce faster lather, facilitate easier rinsing, and/or mitigate harshness on the keratinous tissue. The co-surfactant further may aid in producing lather having more desirable texture, volume and/or other properties.

Amphoteric surfactants suitable for use herein include, but are not limited to derivatives of aliphatic secondary and tertiary amines in which the aliphatic radical can be straight or branched chain and wherein one substituent of the aliphatic substituents contains from about 8 to about 18 carbon atoms and one contains an anionic water solubilizing group, e.g., carboxy, sulfonate, sulfate, phosphate, or phosphonate. Examples include sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products described in U.S. Pat. No. 2,528,378, and mixtures thereof.

The amphoteric surfactants may selected from the family of betaines such as lauryolamphoacetate.

Zwitterionic surfactants suitable for use herein include, but are not limited to derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one substituent contains an anionic group, e.g., carboxy, sulfonate, sulfate, phosphate, or phosphonate. Other zwitterionic surfactants suitable for use herein include betaines, including high alkyl betaines such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, and mixtures thereof. The sulfobetaines may include coco dimethyl sulfopropyl betaine, stearyl dimethyl sulfopropyl betaine, lauryl dimethyl sulfoethyl betaine, lauryl bis-(2-hydroxyethyl) sulfopropyl betaine and mixtures thereof. Other suitable amphoteric surfactants include amidobetaines and amidosulfobetaines, wherein the RCONH($CH_2$)$_3$ radical, wherein R is a $C_{11}$-$C_{17}$ alkyl, is attached to the nitrogen atom of the betaine.

Nonionic co-surfactants suitable for use in the composition for enhancing lather volume or texture include water soluble materials like lauryl dimethylamine oxide, cocodimethylamine oxide, cocoamidopropylamine oxide, laurylamidopropyl amine oxide, etc. or alkylpolyethoxylates like laureth-4 to laureth-7 and water insoluble components such as cocomonoethanol amide, cocodiethanol amide, lauroyl-monoethanol amide, alkanoyl isopropanol amides, and fatty alcohols like cetyl alcohol and oleyl alcohol, and 2-hydroxyalkyl methyl ethers, etc.

Further suitable materials as co-surfactants herein include 1,2-alkylepoxides, 1,2-alkanediols, branched or straight chain alkyl glyceryl ethers (e.g., as disclosed in EP 1696023A1), 1,2-alkylcyclic carbonates, and 1,2-alkyl cyclicsulfites, particularly those wherein the alkyl group contains 6 to 14 carbon atoms in linear or branched configuration. Other examples include the alkyl ether alcohols derived from reacting $C_{10}$ or $C_{12}$ alpha olefins with ethylene glycol (e.g., hydroxyethyl-2-decyl ether, hydroxyethyl-2-dodecyl ether), as can be made according to U.S. Pat. Nos. 5,741,948; 5,994,595; 6,346,509; and 6,417,408.

Other nonionic surfactants may be selected from the group consisting of glucose amides, alkyl polyglucosides, sucrose cocoate, sucrose laurate, alkanolamides, ethoxylated alcohols and mixtures thereof. The nonionic surfactant is selected from the group consisting of glyceryl monohydroxystearate, isosteareth-2, trideceth-3, hydroxystearic acid, propylene glycol stearate, PEG-2 stearate, sorbitan monostearate, glyceryl laurate, laureth-2, cocamide monoethanolamine, lauramide monoethanolamine, and mixtures thereof.

The co-surfactant can be selected from the group consisting of Cocomonoethanol Amide, Cocoamidopropyl Betaine, Laurylamidopropyl Betaine, Cocobetaine, lauryl betaine, lauryl amine oxide, sodium lauryl amphoacetate; alkyl glyceryl ethers, alkyl-di-glyceryl ethers, 1,2-alkyl cyclic sulfites, 1,2-alkyl cyclic carbonates, 1,2-alkyl-epoxides, alkyl glycidylethers, and alkyl-1,3-dioxolanes, wherein the alkyl group contains 6 to 14 carbon atoms in linear or branched configuration; 1,2-alkane diols where the total carbon content is from 6 to 14 carbon atoms linear or branched, methyl-2-hydroxy-decyl ethers, hydroxyethyl-2-dodecyl ether, hydroxyethyl-2-decyl ether, and mixtures thereof.

Cationic surfactants may be derived from amines that are protonated at the pH of the formulation, e.g. bis-hydroxyethyl lauryl amine, lauryl dimethylamine, lauroyl dimethyl amidopropyl amine, cocoylamidopropyl amine, and the like. The cationic surfactants may also be derived from fatty quaternary ammonium salts such as lauryl trimethylammonium chloride and lauroylamidopropyl trimethyl ammonium chloride.

Alkylamphoacetates are suitable surfactants used in the compositions herein for improved product mildness and lather. The most commonly used alkylamphoacetates are lauroamphoacetate and cocoamphoacetate. Alkylamphoacetates can be comprised of monoacetates and diacetates. In some types of alkylamphoacetates, diacetates are impurities or unintended reaction products. However, the presence of diacetate can cause a variety of unfavorable composition characteristics when present in amounts over 15% of the alkylamphoacetates.

Suitable nonionic surfactants for use herein are those selected from the group consisting of glucose amides, alkyl polyglucosides, sucrose cocoate, sucrose laurate, alkanolamides, ethoxylated alcohols and mixtures thereof. In one embodiment the nonionic surfactant is selected from the group consisting of glyceryl monohydroxystearate, isosteareth-2, trideceth-3, hydroxystearic acid, propylene glycol stearate, PEG-2 stearate, sorbitan monostearate, glyceryl laurate, laureth-2, cocamide monoethanolamine, lauramide monoethanolamine, and mixtures thereof.

Non-limiting examples of suitable structurants are described in U.S. Pat. No. 5,952,286, and include unsaturated and/or branched long chain ($C_8$-$C_{24}$) liquid fatty acids or ester derivative thereof; unsaturated and/or branched long chain liquid alcohol or ether derivatives thereof, and mixtures thereof. The surfactant also may comprise short chain saturated fatty acids such as capric acid and caprylic acid. Without being limited by theory, it is believed that the unsaturated part of the fatty acid of alcohol or the branched part of the fatty acid or alcohol acts to "disorder" the surfactant hydrophobic chains and induce formation of lamellar phase. Examples of suitable liquid fatty acids include oleic acid, isostearic acid, linoleic acid, linolenic acid, ricinoleic acid, elaidic acid, arichidonic acid, myristoleic acid, palmitoleic acid, and mixtures thereof. Examples of suitable ester derivatives include propylene glycol isostearate, propylene glycol oleate, glyceryl isostearate, glyceryl oleate, polyglyceryl diisostearate and mixtures thereof. Examples of alcohols include oleyl alcohol and isostearyl alcohol. Examples of ether derivatives include isosteareth or oleth carboxylic acid; or isosteareth or oleth alcohol. The structuring agent may be defined as having melting point below about 25° C.

If present, the composition may comprise a rheology modifier, wherein said rheology modifier comprises cellulosic rheology modifiers, cross-linked acrylates, cross-linked maleic anhydride co-methylvinylethers, hydrophobically modified associative polymers, or a mixture thereof.

An electrolyte, if used, can be added per se to the composition or it can be formed in situ via the counterions included in one of the raw materials. The electrolyte may include an anion comprising phosphate, chloride, sulfate or citrate and a cation comprising sodium, ammonium, potassium, magnesium or mixtures thereof. The electrolyte may be sodium chloride, ammonium chloride, sodium or ammonium sulfate. The electrolyte may be added to the composition in the amount of from about 0.1 wt % to about 15 wt % by weight, alternatively from about 1 wt % to about 6 wt % by weight, and alternatively from about 3 wt % to about 6 wt %, by weight of the composition.

Aqueous Carrier

The cleansing compositions may comprise an aqueous carrier. Typically, the compositions are in the form of pourable liquids (under ambient conditions). The compositions, therefore, comprise an aqueous carrier at a level of at least about, alternatively from about 20% to about 95%, and alternatively from about 60% to about 85%, by weight of the compositions. The aqueous carrier may comprise water, or a miscible mixture of water and organic solvent. The aqueous carrier may also comprise water with minimal or no significant concentrations of organic solvent, except as otherwise incidentally incorporated into the composition as minor ingredients of other components.

Additional Components

The cleansing compositions may further comprise one or more optional components known for use in hair care or personal care products, provided that the optional components are physically and chemically compatible with the components described herein, or do not otherwise unduly impair product stability, aesthetics or performance. Individual concentrations of such optional components may range from about 0.001% to about 10% by weight of the compositions.

Non-limiting examples of optional components for use in the composition include cationic polymers, conditioning agents (hydrocarbon oils, fatty esters, silicones), anti-dandruff agents, suspending agents, viscosity modifiers, dyes, nonvolatile solvents or diluents (water soluble and insoluble), pearlescent aids, foam boosters, additional surfactants or nonionic co-surfactants, pediculocides, pH adjusting agents, perfumes, preservatives, chelants, proteins, skin active agents, sunscreens, UV absorbers, and vitamins.

A. Dispersed Particles

The composition may include dispersed particles. Particles useful can be inorganic, synthetic, or semi-synthetic in origin. If present, dispersed particles are incorporated in an amount from about 0.025% to about 20%, alternatively from about 0.05% to about 10%, alternatively from about 0.1% to about 5%, alternatively from about 0.25% to about 3%, and alternatively from about 0.5% to about 2%, by weight of the composition.

B. Nonionic Polymers

Polyalkylene glycols having a molecular weight of more than about 1000 are useful herein. Useful are those having the following general formula:

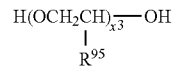

wherein $R^{95}$ is selected from the group consisting of H, methyl, and mixtures thereof. Polyethylene glycol polymers useful herein are PEG-2M (also known as Polyox WSR® N-10, which is available from Union Carbide and as PEG-2,000); PEG-5M (also known as Polyox WSR® N-35 and Polyox WSR® N-80, available from Union Carbide and as PEG-5,000 and Polyethylene Glycol 300,000); PEG-7M (also known as Polyox WSR® N-750 available from Union Carbide); PEG-9M (also known as Polyox WSR® N-3333 available from Union Carbide); and PEG-14 M (also known as Polyox WSR® N-3000 available from Union Carbide).

C. Additional Conditioning Agents

The compositions may also comprise one or more conditioning agents which are in addition to the conditioning delivered by the discrete particles. Conditioning agents include materials which are used to give a particular conditioning benefit to hair and/or skin. The conditioning agents useful in the compositions typically comprise a water-insoluble, water-dispersible, non-volatile, liquid that forms emulsified, liquid particles. Suitable conditioning agents for use in the composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix.

The cleansing composition may further comprise a non-volatile silicone oil. For an opaque composition embodiment, the cleansing composition comprises a non-volatile silicone oil having a particle size as measured in the cleansing composition from about 1 µm to about 50 µm. The cleansing composition may also comprise a non-volatile silicone oil having a particle size as measured in the cleansing composition from about 100 nm to about 1 µm. For a substantially clear composition embodiment, the cleansing composition may comprise a non-volatile silicone oil having a particle size as measured in the cleansing composition of less than about 100 nm.

When present, the one or more conditioning agents are in an amount from about 0.01% to about 10%, alternatively from about 0.1% to about 8%, and alternatively from about 0.2% to about 4%, by weight of the composition.

The conditioning agents may be present in the discrete particle, or may be added to the final cleansing composition as a separate component such that they are present primarily in the continuous phase of the cleansing.

D. Anti-Dandruff Actives

The compositions may also contain an anti-dandruff active. Suitable non-limiting examples of anti-dandruff actives include pyridinethione salts, azoles, selenium sulfide, particulate sulfur, keratolytic agents, piroctone olamine and mixtures thereof. Such anti-dandruff actives should be physically and chemically compatible with the components of the composition, and should not otherwise unduly impair product stability, aesthetics or performance.

When present in the composition, the anti-dandruff active is included in an amount from about 0.01% to about 5%, alternatively from about 0.1% to about 3%, and alternatively from about 0.3% to about 2%, by weight of the composition.

E. Humectants

The compositions may contain a humectant. The humectants herein are selected from the group consisting of polyhydric alcohols, water soluble alkoxylated nonionic polymers, and mixtures thereof. The humectants, when used herein, may be present in an amount by weight of the composition from about 0.1% to about 20%, alternatively from about 0.5% to about 5%.

F. Structurants and Suspending Agent

The compositions may further comprise a structurant or suspending agent at concentrations effective for suspending water-insoluble material in dispersed form in the compositions or for modifying the viscosity of the composition. Such concentrations range from about 0.02% to about 10%, alternatively from about 0.02% to about 5.0%, alternatively from about 0.02% to about 1.5% by weight of the composition.

Suspending agents useful herein include crystalline suspending agents which can be categorized as acyl derivatives, long chain amine oxides, and mixtures thereof. These suspending agents are described in U.S. Pat. No. 4,741,855. These suspending agents may include ethylene glycol esters of fatty acids having from about 16 to about 22 carbon atoms. Alternatives include ethylene glycol stearates, both mono and distearate, and the distearate containing less than about 7% of the mono stearate.

The use of hydrogenated castor oil structurant (such as commercial name: Thixcin R, supplied by Elementis Specialties) can assist with the formulation using higher levels of fatty amphiphile, such as fatty alcohol in the gel network. The use of hydrogenated castor oil results in improved formulation flexibility by producing (i) a dispersion having high concentration of the structurant (more efficient use of the plant vessels), and (ii) a crystal habit/form that results in a higher yield stress in the final product, imparting high stability, for a given amount structurant.

G. Other Optional Components

The compositions may contain other optional components. Optional components may be present in the dispersed gel network phase or may be added to the final cleansing composition as separate components.

For example, the compositions may contain water-soluble and water-insoluble vitamins such as vitamins B1, B2, B6, B12, C, pantothenic acid, pantothenyl ethyl ether, panthenol, biotin and their derivatives, and vitamins A, D, E, and their derivatives. The compositions may also contain water-soluble and water-insoluble amino acids such as asparagine, alanine, indole, glutamic acid and their salts, and tyrosine, tryptamine, lysine, histadine and their salts. The compositions may further comprise materials useful for hair loss prevention and hair growth stimulants or agents.

Any other suitable optional component can also be included in the composition, such as those ingredients that are conventionally used in given product types. The CTFA Cosmetic Ingredient Handbook, Tenth Edition (2004), published by the Cosmetic, Toiletry, and Fragrance Association, Inc., Washington, D.C., describes a wide variety of nonlimiting materials that can be added to the composition herein. Examples of these ingredient classes include, but are not limited to: abrasives, absorbents, aesthetic components such as perfumes and fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antibacterial agents, antifungal agents, antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, plant derivatives, plant extracts, plant tissue extracts, plant seed extracts, plant oils, botanicals, botanical extracts, preservatives, propellants, reducing agents, sebum control agents, sequestrants, skin bleaching and lightening agents, (e.g., hydroquinone, kojic acid, ascorbic acid, magnesium ascorbyl phosphate, ascorbyl glucoside, pyridoxine), enzymes, coenzymes, skin-conditioning agents (e.g., humectants and occlusive agents), skin soothing and/or healing agents and derivatives (e.g., panthenol, and derivatives such as ethyl panthenol, aloe vera, pantothenic acid and its derivatives, allantoin, bisabolol, and dipotassium glycyrrhizinate), skin treating agents (e.g., vitamin D compounds, mono-, di-, and tri-terpenoids, beta-ionol, cedrol), thickeners (including a mono- or divalent salt such as sodium chloride), and vitamins, their derivatives, and combinations thereof.

Test Methods

Hair Substrate

Four grams, 8 inch Caucasian source untreated hair tresses (i.e. no chemical treatment) sourced from International Hair Importers & Products Inc.

Hair Treatment

Hair tresses are hung over a sink and pre-wetted with water for about 30 seconds. The tresses are then sandwiched between one's index and middle fingers and pulled through the fingers to remove excess water. 0.4 cc of cleansing composition is applied to the front side of each hair tress, in a zig-zag manner down the length of each switch. The cleansing is brushed into each hair tress, for about 30 seconds, using a small, Goody®, stiff-bristle, plastic brush. Each hair tress is then rinsed with water for about 30 seconds. The tresses are then sandwiched between one's index and middle fingers and pulled through the fingers to remove excess water. The hair tresses are then flipped over and 0.4 cc of cleansing composition is applied to the back side of each hair tress, in a zig-zag manner down the length of each tress. Each hair tress is then rinsed with water for about 30 seconds. The tresses are then sandwiched between one's index and middle fingers and pulled through the fingers to remove excess water. The hair tresses are then air-dried. Water used for pre-wetting and rinsing hair tresses is typically at a temperature of about 100° F. and a pressure of about 1.5 gal/min. The water is typically at a hardness of about 7 grains/gallon to about 13 grains/gallon. Following hair treatment, the hair tresses are placed in a hot box at 80° C. until the hair is dry.

Cetyl Alcohol Quantitation

Hair samples are equilibrated in a 20% RH constant humidity chamber overnight. For each sample, 0.1 g of hair are cut in 20-40 mm segments into vials (n=4). First, the hair is extracted gently with hexane to remove the external cetyl alcohol. The hexane extraction consists of extracting the hair with hexane two times and then concentrating the dried residue in a second solvent (mobile phase for the Supertcritical Fluid Chromatography-Mass Spectrometry (SFC-MSMS) and N,O-bis(trimethylsilyl trifluoroacetamide (BSTFA) derivatizing reagent for the Gas Chromatography (GC). Next, the internal cetyl alcohol is extracted using 2:1 and then 1:1 chloroform:methanol. The chloroform contains 10 mM dimethylhexylamine (DMHA) and the methanol 1% formic acid. Each extraction is heated for 30 minutes at 65° C. with the hair and then combined and the dried residue re-dissolved in a second solvent (mobile phase for the SFCMS-MS and BSTFA derivatizing reagent for the GC). Cetyl alcohol is quantified by gas chromatography with flame ionization detection using a polydimethylsiloxane capillary column with hydrogen mobile phase. Nonadecanoic acid and eicosanoic acid are used as internal standards.

SAXS/WAXS X-Ray Sample Prep/Procedure

A single bead is dropped into the flared end of a 2.5 mm OD capillary (0.01 mm wall thickness) containing the cleansing chassis, pressing gently into the neck of the capillary to ensure it is fully submerged. This prep is used for each of the time points collected, centering the location of the capillary containing the bead in the sample beam so as to capture the SAXS pattern of the bead itself as it changed over time. Though the beads are slightly larger than the bodies of the capillaries, the gradual flare leading to their open end allowed for their size kept the beads in place for an entire day of analyses.

The 18×0129 bead is removed from its capillary after a day and its WAXS pattern is collected. Sample 18×0130 currently remains in its capillary with the cleansing chassis in case a longer time scale analysis is needed.

The instrumentation used in the X-ray diffraction measurement includes the following: 1) Small angle data (SAXS) is a Bruker NanoSTAR (Billerica, Mass., USA) small-angle X-ray scattering instrument. The microfocus Cu X-ray tube is operated at 50 kV, 0.60 mA with 550 micrometer ScanTex Pinholes. The sample to detector distance is 109.260 cm and the detector a Vantec2K two-dimensional area detector. Samples are placed in the solid sample holder and analyzed under atmospheric conditions with an analysis time of 1200. 2) Wide-angle data (WAXS) are collected on a Stoe STADI-P transmission mode diffractometer. The generator is operated at 40 kV/50 mA, powering a copper anode long-fine-focus Cu X-ray tube. The diffractometer incorporates an incident-beam curved germanium-crystal monochromator, standard incident-beam slit system and an image plate-position sensitive detector with an angular range of about 124_ 2 h. Data are collected in transmission mode over a range of 0 to 124_ 2 h for 900 s.

Compression Measurement of Swollen Discrete Particle

It is desirable that, once incorporated into finished product, the discrete particle sufficiently swells or "hydrates", therein allowing the particle to begin to blend with the cleansing continuous phase as the product is dispensed from the package by the consumer. FIG. 1 depicts particle hydration. FIG. 1 includes the anhydrous particle 10, and the discrete particle 12. It results in different domains of hydration within the particle structure as a function of time and particle and chassis composition 14. The different domains are described as follows:

Unhydrated Solid Phase 16=least hydrated phase of the discrete particle, which phase most resembles the anhydrous particle, having experienced little if any significant hydration, such that the compression of which phase is equal to or exceeds the 50 g force limitation of the Kawabata KES-FB3-Auto Compression Test method as described herein.

Semi-Hydrated Gel Phase 18=partially hydrated phase of the discrete particle, which continues to hydrate over time and the compression of which phase is measurable using the Kawabata KES-FB3-Auto Compression Tester and corresponding methodology described hereafter.

Hydrated Gel Phase 20=most hydrated phase of the discrete particle that on a micro scale most closely resembles a dispersed gel network phase.

A method described herein, characterizes the degree to which the discrete particles (referred to hereafter as "particles" or "beads") have softened in product. This method employs the Kawabata KES-FB3-Auto Compression Tester, which is manufactured by Kato Tech, LTD, or like equipment. Following, are the equipment settings employed herein for the Kawabata KES-FB3-Auto Compression Tester—Sensitivity: 2, Velocity: 0.02 mm/sec, Stroke 10, Zone or Probe Compression Area: 2 (corresponds to a standard 16 mm compression probe), Process Rate: 0.1, Maximum Load: 50 gf/cm2.

Figure 2:
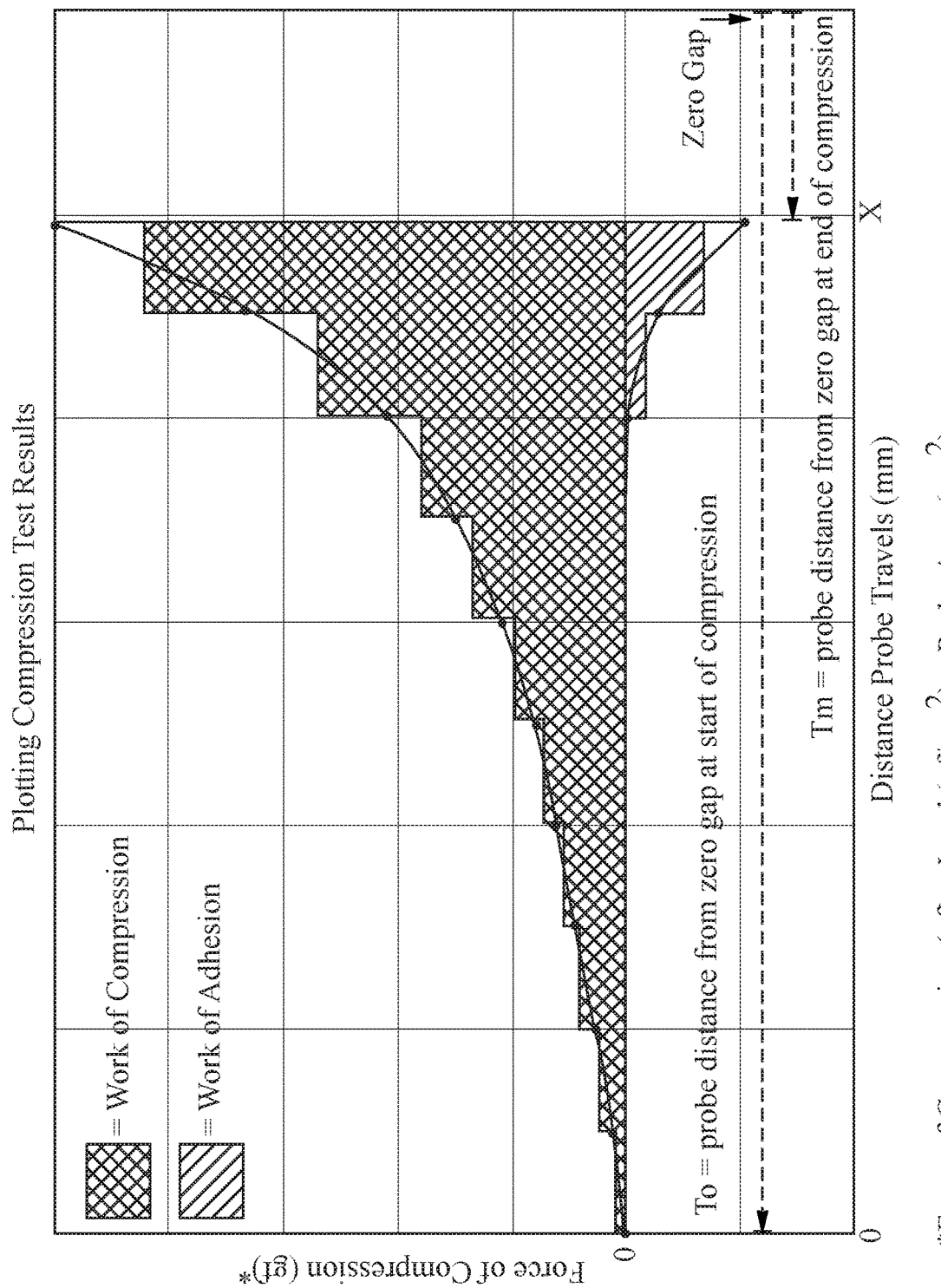
FIG. 2 is a graph of compression test results.
Figure 3:
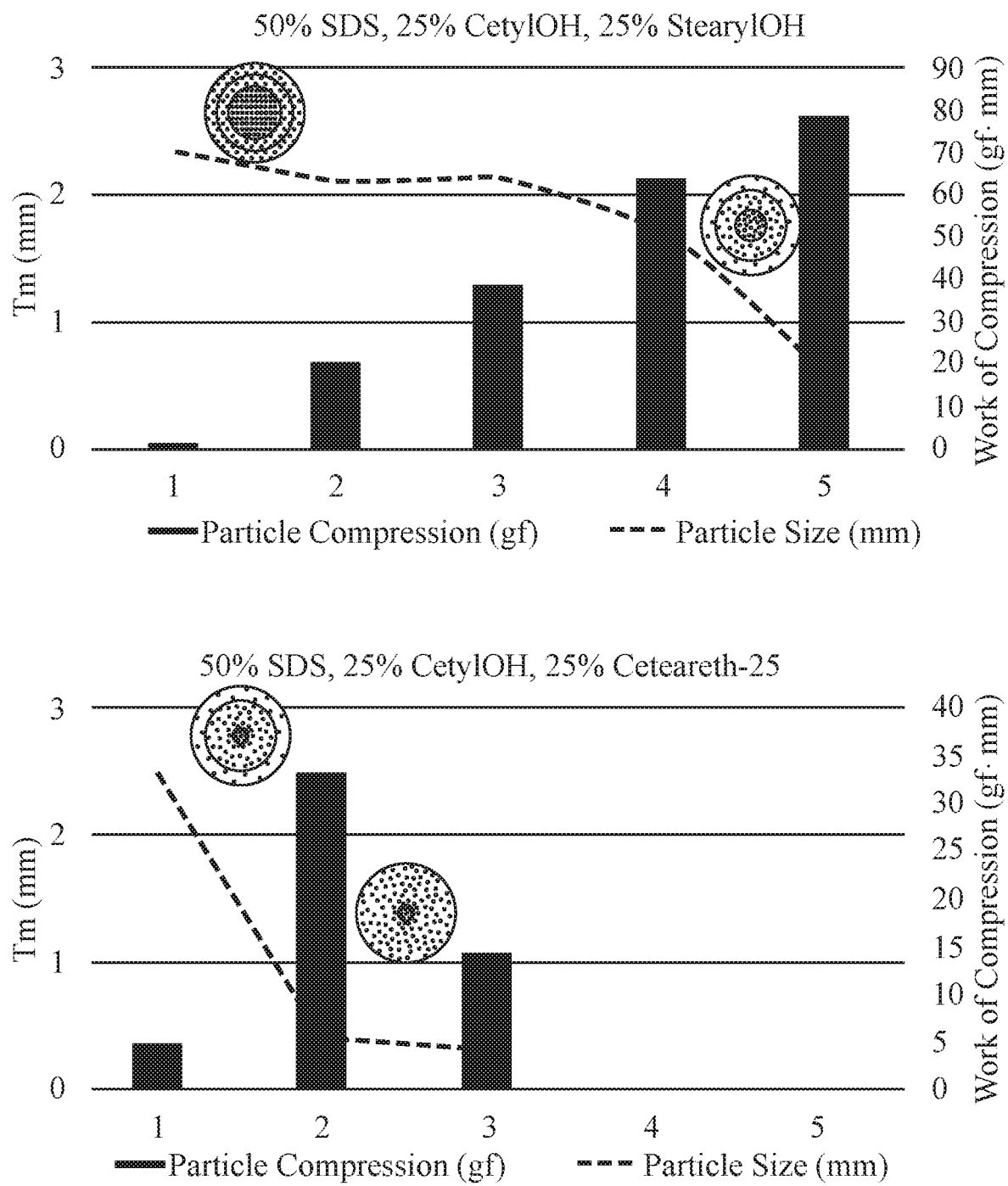
FIG. 3 is a graph of particle compression and size over time.

Example data resulting from this method are included in Tables 1 and 2 below and are used to calculate (1) the Total Work of Compression [$WC_{total}$] incurred in compressing the semi-hydrated gel phase (depicted in FIG. 2 below) and (2) the size of the unhydrated solid phase remaining [≈Tm (mm)] at a specific point in time. These data herein may be used to create a graphical representation or "fingerprint" that describes the degree of hydration of a given bead in product over time (FIG. 3). The following equations may be used to calculate $WC_{total}$, wherein 1) "n" and "n−1" refers to the step number in the particle compression measurement from which the corresponding data is obtained and n≥2, 2) "FC" refers to the Force of Compression [=Load (gf/cm$_2$)×Probe Compression Area (cm$_2$)] and 3) "D" refers to the Probe Travel Distance:

$$WC_{total} = \Sigma(FC_{avg}) \cdot (\Delta D)$$

Example data analysis:

$$WC_{total} = \sum_{n=2}^{10} \frac{(FC_n + FC_{n-1})}{2} \cdot (D_n - D_{n-1})$$

TABLE 1

| Measurement Step No. | Probe Travel Distance, D (mm) | Load (gf/cm$^2$) | Force of Compression, FC (gf) | Work of Compression, WC (gf · mm) |
|---|---|---|---|---|
| 1 | 0.0 | 0.0 | 0.0 | 0.2 |
| 2 | 0.2 | 1.1 | 2.1 | 0.6 |
| 3 | 0.4 | 2.0 | 4.0 | 1.0 |
| 4 | 0.6 | 3.2 | 6.4 | 1.6 |
| 5 | 0.8 | 4.9 | 9.8 | 2.4 |
| 6 | 1.0 | 7.3 | 14.6 | 4.5 |
| 7 | 1.2 | 15.0 | 30.1 | 6.4 |
| 8 | 1.4 | 17.2 | 34.4 | 8.5 |
| 9 | 1.6 | 25.3 | 50.6 | 14.3 |
| 10 | 1.8 | 46.3 | 92.7 | |

TABLE 2

| Probe Compression Area (cm$^2$) | Initial Sample Thickness, To (mm) | Final Sample Thickness, Tm (mm) | Distance Probe Travels, To-Tm (mm) | Total Work of Compression (gf · mm) |
|---|---|---|---|---|
| 2 | 2.2 | 0.4 | 1.8 | 39.7 |

Sample Preparation for Compression Measurement

Product samples are prepared for measurement by incorporating beads into finished product (e.g. at a ratio of about 10 beads into about 5 grams of cleansing composition such as a shampoo) such that the beads are effectively coated by product. These beads are sampled from product one at a time at various time intervals using a small spatula, taking care not to deform the beads during extraction. Without being limited to a specific time scale, bead compression is performed at the following time intervals (hrs): 0, 1, 3, 6 and 24 hours. Following proper equipment calibration and measurement set-up, a bead is carefully extracted from product and centered on the sample stage of the KES-FB3-A Compression Tester, beneath the compression probe, in preparation for sample analysis.

NON-LIMITING EXAMPLES

The compositions illustrated in the following Examples illustrate specific embodiments of the composition, but are not intended to be limiting thereof. Other modifications can be undertaken by the skilled artisan without departing from the spirit and scope of this invention. These exemplified embodiments of the composition as described herein provide enhanced conditioning benefits to the hair.

All exemplified amounts are listed as weight percents and exclude minor materials such as diluents, preservatives, color solutions, imagery ingredients, botanicals, and so forth, unless otherwise specified. All percentages are based on weight unless otherwise specified.

The following Examples illustrate specific embodiments of the anhydrous particles prior to its incorporation with the other components of the final cleasning composition. It is intended that each of the following anhydrous particle premix examples could be incorporated as a discrete particle into a cleansing composition such as a shampoo composition.

| Ingredient | P Ex 1 | P Ex 2 | P Ex 3 | P Ex 4 | P Ex 5 | P Ex 6 | P Ex 7 |
|---|---|---|---|---|---|---|---|
| Water | | | | | | | |
| Glyceryl Palmitate [1] | | | | | | 38% | |
| PEG-5 Glyceryl Stearate [1] | | | | | | 37% | |
| Sorbitan Tristearate [1] | 75% | | | | | | |
| Stearamide MEA-Stearate [1] | | 75% | | | | | |
| Steareth-2, Brij ™ S2 [2] | | | 75% | | | | 55% |
| Lauric Acid, Lauric Acid-PrimG [3] | | | | 75% | | | 20% |
| Sucrose Distearate, Crodesta F-10 [2] | | | | | 75% | | |
| Behenyltrimethylammonium Chloride, Genamin KDMP [4] | 25% | 25% | 25% | 25% | 25% | 25% | 25% |

| Ingredient | P Ex 8 | P Ex 9 | P Ex 10 | P Ex 11 | P Ex 12 | P Ex 13 | P Ex 14 |
|---|---|---|---|---|---|---|---|
| Water | | | | | | | |
| Glyceryl Stearate [22] | 38% | | | | | | |
| SEFA Stearate, Sefose-1618H [5] | | 50% | | | | | |
| Cetyl Alcohol | | | 25% | 25% | 25% | | 25% |
| Stearyl Alcohol | | | 25% | 25% | | 25% | |
| Laureth-23 | 12% | | | | 25% | | |
| Ceteareth-25 | | | | 25% | | | 25% |
| Oleic Acid | | | | | | 25% | |
| Sodium Dodecyl Sulfate, ≥95% [6] | 50% | 50% | 50% | 25% | 50% | 50% | 50% |

-continued

| Ingredient | P Ex 15 | P Ex 16 | P Ex 17 | P Ex 18 | P Ex 19 | P Ex 20 | P Ex 21 |
|---|---|---|---|---|---|---|---|
| Water | 10% | | | | | | |
| Benzyl Alcohol | | | 6% | | | | |
| Lauryl Alcohol | | 10% | | | | | |
| Cetyl Alcohol | 20% | | 14% | 45% | 30% | 36% | 20% |
| Stearyl Alcohol | 30% | 10% | 34% | | | | 20% |
| Ceteareth-25 | | | | 40% | 10% | 12% | |
| Sodium Dodecyl Sulfate, ≥95% [6] | 40% | | | 15% | 48% | 49% | 60% |
| Behentrimonium Methosulfate [7] | | | 40% | | | | |
| Stearamidopropyl Dimethylamine [8] | | 60% | | | | | |
| Cosmetic Pigment (Mica, Titanium Dioxide, Tin Oxide, Carmine) [9] | | | | | 2% | 1% | |
| Titanium Dioxide (and Alumina) [10] | | | | | | 2% | |
| Glycerin | | 20% | | | 10% | | |
| Fragrance | | | 6% | | | | |

| Ingredient | P Ex 22 | P Ex 23 | P Ex 24 | P Ex 25 | P Ex 26 | P Ex 27 | P Ex 28 |
|---|---|---|---|---|---|---|---|
| Water | 14% | | | | | | |
| Cetyl Alcohol | 20% | 25% | 38% | 38% | | | 38% |
| Stearyl Alcohol | 20% | 25% | 12% | | 25% | 25% | |
| Ceteareth-25 | | | 25% | 8% | 25% | 25% | 10% |
| Sodium Lauryl Sulfate, ≥98% [6] | 36% | 20% | 25% | | 46% | | 50% |
| Sodium Cocoyl Isethionate [11] | | 20% | | | | 48% | |
| Decyl Glucoside, ≥98% [12] | | | | 50% | | | |
| Cosmetic Pigment (Mica, Titanium Dioxide, Iron Oxide) [9] | | | | | 2% | | |
| Dimethicone, Dimethiconol [13, 14, 15] | 10% | 8% | | | | | |
| Polyquaternium-6 [16] | | 2% | | | | | |
| Panthenol [17] | | | | 2% | | | |
| Panthenyl Ethyl Ether [18] | | | | 2% | | | |
| Argan Oil [19] | | | | | 2% | | |
| Coconut Milk [20] | | | | | | 2% | |
| Menthol [21] | | | | | | | 2% |

[1] available from A&E Connock

[2] available from Croda Chemicals

[3] available from Emery Oleochemicals

[4] available from Clariant Int. Ltd.

[5] available from P&G Chemicals

[6] available from Stepan Company

[7] Genamin ® BTMS (Clariant)

[8] Incromine ™ SD (Croda)

[9] PRESTIGE Ruby (Sudarshan Chemical)

[10] Titanium Dioxide (Kobo)

[11] Jordapon Ci-Prilled (BASF)

[12] available from Sigma Aldrich

[13] Cf330m (Momentive Performance Materials)

[14] Belsil ® DM 5500 E (Wacker)

[15] Dow Corning 1872 (Dow Corning Corporation)

[16] Mirapol 100S (Solvay USA Inc.)

[17] DL Panthenol (DSM Nutritional Products Inc)

[18] D/DI Panthenyl Ethyl Ether (DSM Nutritional Products Inc)

[19] Argania Spinosa Kernel Oil (BASF Corporation)

[20] COCONUT MILK 5432472 (IFF)

[21] LAEVO MENTHOL (Symrise)

[22] available from BASF

Discrete Particle Examples 1-4

(GN Ex 1 to GN Ex 4)

Examples of Discrete Particles prior to incorporation with the detersive surfactant and other components of the final cleansing composition.

| Ingredient | GN Ex 1 | GN Ex 2 | GN Ex 3 | GN Ex 4 |
|---|---|---|---|---|
| Water | 78% | 74% | 83% | 80% |
| Stearyl Alcohol | 7% | 7% | 5% | 5% |
| Cetyl Alcohol | 5% | 9% | 3% | 5% |
| Sodium Laureth-1 Sulfate | 11% | 10% | | |
| Behenyltrimethylammonium Chloride, Genamin KDMP [1] | | | 9% | 10% |

[1] available from Clariant Int. Ltd.

Shampoo Examples 1-20

| Ingredient | Ex 1 | Ex 2 | Ex 3 | Ex 4 | Ex 5 | Ex 6 | Ex 7 |
|---|---|---|---|---|---|---|---|
| Sodium Laureth Sulfate [1] | 10.00 | 10.00 | 10.00 | 15.00 | 6.00 | 15.00 | 12.00 |
| Sodium Lauryl Sulfate | 1.50 | 1.50 | 6.00 | | 10.00 | | |
| Cocamidopropyl Betaine | 2.00 | 2.00 | | 1.70 | | 2.00 | |
| Cocamide MEA | | | | | 1.60 | | |
| One or more of the Anhydrous Particle Premixes 1-28 | 1.00 | 5.00 | 1.00 | *5.00 | 10.00 | 20.00 | 2.00 |
| Any one of GN examples 1-4 | 27.30 | 13.60 | 27.30 | *27.30 | | | |
| Zinc Pyrithione | | 1.00 | 1.00 | | | 1.00 | |
| Ketoconazole | | | 1.00 | | | | |
| Climbazole | | 1.50 | | | | | |
| Elubiol | | | | | | 0.25 | |
| Copper Pyrithione | | | | | 1.00 | | |
| Cationic Galactomannan [2] | 0.40 | | 0.40 | | | | |
| Cationic Galactomannan [3] | | 0.10 | | | | | |
| Guar Hydroxypropyl Trimonium Chloride [4] | | | | 0.20 | | 0.20 | |
| Guar Hydroxypropyl Trimonium Chloride [5] | | 0.30 | | | 0.50 | | |
| Polyquaternium-10 [6] | | | | 0.20 | | 0.20 | 0.20 |
| Polyquaternium-6 [7] | | | | 0.10 | 1.00 | 0.10 | |
| Dimethicone [8] | 2.00 | 2.00 | 2.00 | | | | |
| Dimethicone [9] | | | | 1.00 | | 1.00 | |
| Dimethicone [10] | | | | | 2.00 | | |
| Ethylene Glycol Distearate | 1.50 | 1.50 | | 1.50 | | 1.50 | |
| Hydrogenated Castor Oil [11] | | | | | 0.10 | | |
| Acrylates Copolymer [12] | | | 1.50 | | | | |
| Acrylates Crosspolymer-4 [15] | | | | | | | 2.60 |
| 5-Chloro-2-methyl-4-isothiazolin-3-one, Kathon CG | 0.0005 | 0.0005 | 0.0005 | 0.0005 | 0.0005 | 0.0005 | 0.0005 |
| Sodium Benzoate | 0.25 | 0.25 | 0.25 | 0.25 | 0.25 | 0.25 | 0.25 |
| Tetrasodium EDTA | 0.16 | | | 0.16 | | 0.16 | 0.16 |
| Benzyl Alcohol | | 0.03 | 0.03 | | 0.03 | | |
| Perfume | 0.70 | 0.70 | 0.70 | 0.70 | 0.70 | 0.70 | 1.40 |
| Citric Acid/Sodium Citrate Dihydrate/HCl/NaOH | pH QS | pH QS | pH QS | pH QS | pH QS | pH QS | pH QS |
| Sodium Chloride/Ammonium Xylene Sulfonate | Visc. QS | Visc. QS | Visc. QS | Visc. QS | Visc. QS | Visc. QS | Visc. QS |
| Water | QS | QS | QS | QS | QS | QS | QS |

| Ingredient | Ex 8 | Ex 9 | Ex 10 | Ex 11 | Ex 12 | Ex 13 | Ex 14 |
|---|---|---|---|---|---|---|---|
| Sodium Laureth-1 Sulfate | 15.00 | 15.00 | 15.00 | 15.00 | 15.00 | 15.00 | 15.00 |
| Cocamidopropyl Betaine | 2.00 | 2.00 | 2.00 | 2.00 | 2.00 | 2.00 | 2.00 |
| Anhydrous Particle Premix—Example 8 | 5.00 | | | | | | |
| Anhydrous Particle Premix—Example 10 | | 5.00 | | | | | |
| Anhydrous Particle Premix—Example 12 | | | 5.00 | | | | |
| Anhydrous Particle Premix—Example 13 | | | | 5.00 | | | |
| Anhydrous Particle Premix—Example 14 | | | | | 3.60 | 9.20 | |
| Anhydrous Particle Premix—Example 22 | | | | | | | 5.00 |
| Guar Hydroxypropyl Trimonium Chloride [13] | 0.15 | 0.15 | 0.15 | 0.15 | 0.15 | 0.15 | 0.15 |
| Polyquaternium-10 [6] | 0.15 | 0.15 | 0.15 | 0.15 | 0.15 | 0.15 | 0.15 |
| 5-Chloro-2-methyl-4-isothiazolin-3-one, Kathon CG | 0.0005 | 0.0005 | 0.0005 | 0.0005 | 0.0005 | 0.0005 | 0.0005 |
| Sodium Benzoate | 0.25 | 0.25 | 0.25 | 0.25 | 0.25 | 0.25 | 0.25 |
| Tetrasodium EDTA | 0.16 | | | 0.16 | | 0.16 | 0.16 |
| Perfume | 0.70 | 0.70 | 0.70 | 0.70 | 0.70 | 0.70 | 1.20 |
| Citric Acid/Sodium Citrate Dihydrate | pH QS | pH QS | pH QS | pH QS | pH QS | pH QS | pH QS |
| Sodium Chloride/Ammonium Xylene Sulfonate | Visc. QS | Visc. QS | Visc. QS | Visc. QS | Visc. QS | Visc. QS | Visc. QS |
| Water | QS | QS | QS | QS | QS | QS | QS |
| Size of Anhydrous Particle (mm) | 3.19 | 2.38 | 3.87 | 2.59 | 2.64 | | 4.15 |
| Size of Unhydrated Solid Phase @ 6 hrs in SH (mm) | 0.30 | 1.57 | 1.17 | 0.30 | Too soft to measure | | 0.53 |

-continued

| | | | | | | | |
|---|---|---|---|---|---|---|---|
| Work of Compression @ 6 hrs in SH (gf•mm) | 55.1 | 37.6 | 61.5 | 55.9 | Too soft to measure | | 90.3 |
| Size of Unhydrated Solid Phase @ 24 hrs in SH (mm) | Too soft to measure | 0.15 | 0.53 | 0.15 | Too soft to measure | | 0.35 |
| Work of Compression @ 24 hrs in SH (gf•mm) | Too soft to measure | 54.5 | 80.4 | 53.4 | Too soft to measure | | 96.3 |
| Cetyl Alcohol Penetration into Hair Fiber (ppm) | | | | | 117 | 155 | |
| X-ray Diffraction Lamellar Structure Basal Spacing @ 20+ hrs in shampoo (Å) | | | 74 | | 94 | | |

| Ingredient | Ex 15 | Ex 16 | Ex 17 | Ex 18 | Ex 19 | Ex 20 | Ex 21 |
|---|---|---|---|---|---|---|---|
| Sodium Laureth-1 Sulfate | 15.00 | 15.00 | 15.00 | 15.00 | 15.00 | 15.00 | 15.00 |
| Cocamidopropyl Betaine | 2.00 | 2.00 | 2.00 | 2.00 | 2.00 | 2.00 | 2.00 |
| Anhydrous Particle Premix—Example 19 | 3.60 | | | 5.00 | 5.00 | | |
| Anhydrous Particle Premix—Example 20 | | 5.00 | | | | 5.00 | 5.00 |
| Anhydrous Particle Premix—Example 24 | | | 5.00 | | | | |
| Guar Hydroxypropyl Trimonium Chloride [13] | | | | | | | |
| Polyquaternium-10 [6] | 0.50 | 0.50 | | | | | |
| Polyquaternium-10 [14] | | | | | | | |
| Dimethicone [10] | | | | | | | |
| Acrylates Copolymer [12] | 1.50 | 1.50 | 2.00 | | 2.00 | | 2.00 |
| 5-Chloro-2-methyl-4-isothiazolin-3-one, Kathon CG | 0.0005 | 0.0005 | 0.0005 | 0.0005 | 0.0005 | 0.0005 | 0.0005 |
| Sodium Benzoate | 0.25 | 0.25 | 0.25 | 0.25 | 0.25 | 0.25 | 0.25 |
| Tetrasodium EDTA | 0.16 | | | 0.16 | | 0.16 | 0.16 |
| Perfume | 0.70 | 0.70 | 0.70 | 0.70 | 0.70 | 0.70 | 1.20 |
| Citric Acid/Sodium Citrate Dihydrate | pH QS | pH QS | pH QS | pH QS | pH QS | pH QS | pH QS |
| Sodium Chloride/Ammonium Xylene Sulfonate | Visc. QS | Visc. QS | Visc. QS | Visc. QS | Visc. QS | Visc. QS | Visc. QS |
| Water | QS | QS | QS | QS | QS | QS | QS |
| Size of Anhydrous Particle (mm) | | | 3.47 | 2.63 | 2.63 | 2.53 | 2.53 |
| Size of Unhydrated Solid Phase @ 6 hrs in SH (mm) | | | 0.60 | 0.14 | 0.35 | 0.26 | 0.48 |
| Work of Compression @ 6 hrs in SH (gf · mm) | | | 79.5 | 27.9 | 65.0 | 53.1 | 75.0 |

| Ingredient | Ex 22 | Ex 23 | Ex 24 | Ex 25 | Ex 26 | Ex 27 | Ex 28 |
|---|---|---|---|---|---|---|---|
| Sodium Laureth-1 Sulfate | 15.00 | 15.00 | 15.00 | 15.00 | 15.00 | 15.00 | 15.00 |
| Cocamidopropyl Betaine | 2.00 | 2.00 | 2.00 | 2.00 | 2.00 | 2.00 | 2.00 |
| Any one or combination of Anhydrous Particle Premixes 1-28 | 1.00 | 5.00 | 1.00 | 5.00 | 10.00 | 15.00 | 30.00 |
| Guar Hydroxypropyl Trimonium Chloride [13] | 0.15 | 0.30 | | | 0.30 | | 0.10 |
| Polyquaternium-10 [6] | 0.15 | | 0.50 | | | 0.80 | 0.10 |
| Polyquaternium-10 [14] | | | | | 0.30 | | |
| Dimethicone [10] | | 2.00 | | 4.00 | | | 1.00 |
| Acrylates Copolymer [12] | 1.50 | 1.50 | 1.50 | | 2.00 | | 2.00 |
| 5-Chloro-2-methyl-4-isothiazolin-3-one, Kathon CG | 0.0005 | 0.0005 | 0.0005 | 0.0005 | 0.0005 | 0.0005 | 0.0005 |
| Sodium Benzoate | 0.25 | 0.25 | 0.25 | 0.25 | 0.25 | 0.25 | 0.25 |
| Tetrasodium EDTA | 0.16 | | | 0.16 | | 0.16 | 0.16 |
| Perfume | 0.70 | 0.70 | 0.70 | 0.70 | 0.70 | 0.70 | 1.20 |
| Citric Acid/Sodium Citrate Dihydrate | pH QS | pH QS | pH QS | pH QS | pH QS | pH QS | pH QS |
| Sodium Chloride/Ammonium Xylene Sulfonate | Visc. QS | Visc. QS | Visc. QS | Visc. QS | Visc. QS | Visc. QS | Visc. QS |
| Water | QS | QS | QS | QS | QS | QS | QS |

\* Denotes where anhydrous particle is premixed with gel network prior to addition to shampoo.
[1] Sodium Laureth-n Sulfate, where n ≥ 1 and ≤ 3
[2] Cationic Galactomannan (with Mol. W. of ~200,000; Char. Den. = 3.0 meq/g)
[3] Cationic Galactomannan (with Mol. W. of ~200,000; Char. Den. = 0.7 meq/g)
[4] Jaguar C17 (Rhodia)
[5] ADPP-5043H1VPW (with Mol. W. of ~1,200,000 and Char. Den. of 2.0 meq/g) available from Aqualon/Hercules
[6] Polymer LR30M (Dow Chemical Company)
[7] Mirapol 100S (Solvay USA Inc.)
[8] Cf330m (Momentive Performance Materials)
[9] Belsil ® DM 5500 E (Wacker)
[10] Dow Corning 1872 (Dow Corning Corporation)
[11] Trihydroxystearin-PrimG (Elementis Specialties Inc.)
[12] Carbopol Aqua SF 1 (Lubrizol Advanced Materials)
[13] Jaguar Excel (Solvay)
[14] Polymer KG30M (Dow Chemical Company)
[15] Carbopol Aqua SF 2 (Lubrizol Advanced Materials)

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A cleansing composition comprising:
   (a) a detersive surfactant;
   (b) an aqueous carrier;
   (c) from about 0.5% to about 30% by weight of the cleansing composition of discrete particles comprising anhydrous particles and an aqueous phase, and wherein said anhydrous particles comprise:
   (1) one or more fatty amphiphile selected from the group consisting of fatty alcohol, fatty ester, fatty acid, fatty amide and mixtures thereof; and
   (2) one or more secondary surfactants selected from the group consisting of anionic, nonionic, zwitterionic, cationic or mixtures thereof;
   wherein the discrete particle has a size of 500 microns to 15000 microns, wherein the cleansing composition has a % transmittance of about 75% or higher.

2. The cleansing composition of claim 1, wherein the fatty amphiphile is from about 0.25% to about 15% by weight of the cleansing composition.

3. The cleansing composition of claim 1, wherein the size of the discrete particle is 500 microns to 7000 microns.

4. The composition of claim 1, wherein the anhydrous particle has a size scale of about 1 mm to about 10 mm.

5. The composition of claim 1, wherein the discrete particle is in a semi-hydrated gel phase and has a compression of from about 0.5 gram-force units to about 50 gram-force units as determined using the KES-FB3-A Compression Tester.

6. A cleansing composition comprising:
   (a) a detersive surfactant;
   (b) an aqueous carrier;
   (c) from about 0.5% to about 30% by weight of the cleansing composition of discrete particles comprising anhydrous particles and an aqueous phase, and wherein said anhydrous particles comprise:
   1) at least two fatty amphiphiles selected from the group consisting of fatty alcohol, fatty ester, fatty acid, fatty amide, and mixtures thereof; and
   2) one or more secondary surfactants selected from the group consisting of anionic, nonionic, zwitterionic, cationic or mixtures thereof, wherein the secondary surfactant comprises a hydrophobic tail group with a chain length of 16 to 22 carbon atoms, and wherein a weight ratio of fatty amphiphile to secondary surfactant is 1:5 to 100:1; and
   (d) wherein the discrete particle has a size of 500 microns to 15000 microns, wherein the cleansing composition has a % transmittance of about 75% or higher.

\* \* \* \* \*